US010881860B2

(12) United States Patent
Thompson et al.

(10) Patent No.: US 10,881,860 B2
(45) Date of Patent: Jan. 5, 2021

(54) MRI-SAFE IMPLANTABLE LEAD ASSEMBLY

(71) Applicant: LivaNova USA, Inc., Houston, TX (US)

(72) Inventors: David L. Thompson, Houston, TX (US); Jason F. Lindh, Friendswood, TX (US)

(73) Assignee: LivaNova USA, Inc., Houston, TX (US)

(*) Notice: Subject to any disclaimer, the term of this patent is extended or adjusted under 35 U.S.C. 154(b) by 173 days.

(21) Appl. No.: 15/984,234

(22) Filed: May 18, 2018

(65) Prior Publication Data
US 2018/0264257 A1 Sep. 20, 2018

Related U.S. Application Data

(62) Division of application No. 14/885,794, filed on Oct. 16, 2015, now Pat. No. 9,974,949.

(51) Int. Cl.
A61N 1/365 (2006.01)
A61N 1/375 (2006.01)
A61N 1/37 (2006.01)
A61N 1/02 (2006.01)
A61N 1/05 (2006.01)
A61N 1/08 (2006.01)

(52) U.S. Cl.
CPC ......... *A61N 1/36521* (2013.01); *A61N 1/025* (2013.01); *A61N 1/05* (2013.01); *A61N 1/3718* (2013.01); *A61N 1/3752* (2013.01); *A61N 1/3754* (2013.01); *A61N 1/086* (2017.08)

(58) Field of Classification Search
CPC ............ A61N 1/08; A61N 1/025; A61N 1/05
See application file for complete search history.

(56) References Cited

U.S. PATENT DOCUMENTS

| 7,620,453 | B1 | 11/2009 | Propato et al. | |
| 2005/0043761 | A1 | 2/2005 | Connelly et al. | |
| 2005/0222657 | A1* | 10/2005 | Wahlstrand | A61N 1/0534 607/116 |
| 2007/0106332 | A1 | 5/2007 | Denker et al. | |

(Continued)

OTHER PUBLICATIONS

PCT Application No. PCT/US2016/056893, International Search Report and Written Opinion dated Dec. 23, 2016, 18 pages.

(Continued)

*Primary Examiner* — Joseph M Dietrich
(74) *Attorney, Agent, or Firm* — Foley & Lardner LLP

(57) ABSTRACT

A medical device includes a pulse generator and a filter. The pulse generator is configured to generate a stimulation signal and to provide the stimulation signal to tissue of a patient via an implantable lead assembly. The filter is configured to couple to the implantable lead assembly. A combined impedance of the implantable lead assembly and the filter with respect to a current induced by an external electro-magnetic field satisfies an impedance threshold when the external electro-magnetic field has a first frequency and when the external electro-magnetic field has a second frequency. The combined impedance has a peak impedance value when the external electro-magnetic field has a third frequency that is between the first frequency and the second frequency.

20 Claims, 9 Drawing Sheets

(56) References Cited

U.S. PATENT DOCUMENTS

| | | |
|---|---|---|
| 2011/0112599 A1 | 5/2011 | Zhang et al. |
| 2012/0158078 A1 | 6/2012 | Moulder et al. |
| 2013/0073020 A1 | 3/2013 | Mouchawar et al. |
| 2013/0073021 A1 | 3/2013 | Halperin et al. |

OTHER PUBLICATIONS

PCT Application No. PCT/US2016/056893, Invitation to Pay Additional Fees dated Dec. 23, 2016, 7 pages.
Office Action on European patent application No. 16784748.2 dated Apr. 17, 2019. 6 pages.

\* cited by examiner

MRI-SAFE IMPLANTABLE LEAD ASSEMBLY

CROSS-REFERENCE TO RELATED APPLICATIONS

This application is a divisional application of U.S. application Ser. No. 14/885,794, filed Oct. 16, 2015, which is hereby incorporated by reference herein in its entirety.

FIELD OF THE DISCLOSURE

The present disclosure is generally related to medical devices and implantable lead assemblies and, in particular, to medical devices and lead assemblies exposed to MRI fields.

BACKGROUND

Implantable lead assemblies, coupled to medical devices, are used for a variety of medical purposes, such as gathering patient body parameter data or providing therapy (e.g., electro-stimulation). For example, an implantable lead assembly may be used as part of a system that includes an electrode and a medical device (e.g., an implantable medical device or an external medical device). A surgical procedure may be used to implant at least a portion of the system within tissue of a patient, and removal of the system from the patient may require a second surgical procedure. Accordingly, removal of the system after implantation should be avoided to the extent possible.

If the patient needs certain imaging procedures, such as a magnetic resonance imaging (MRI) procedure, after the system is implanted, it may be preferable to perform the MRI procedure without subjecting the patient to a surgical procedure to remove the system. However, an electro-magnetic field used during the MRI procedure can induce electric currents in portions of the system, such as the implantable lead assembly. A current induced in an implantable lead assembly by an electro-magnetic field of an MRI procedure can be dangerous for the patient. For example, if the current is applied to the tissue of the patient, the current can cause damage or discomfort.

SUMMARY

Accordingly, an MRI-safe medical device system, lead, or component of the present disclosure may be configured to prevent or limit the formation of a current, to dissipate a current, and/or to mitigate the effects of a current induced in an implantable lead assembly or a component thereof by an electro-magnetic field of an MRI procedure. The medical device system, lead, or component may limit or avoid application of the induced current to the tissue of the patient. Additionally, the MRI-safe medical device system, lead, or component may be configured to dissipate induced current in a manner that limits formation of local hotspots as a result of Ohmic heating generated by a magnetic field.

During an MRI procedure, an impedance of an implantable lead assembly of the medical device system, or a component thereof, may be based on a current induced by an electro-magnetic field caused by the MRI procedure. According to a particular embodiment, the implantable lead assembly may include at least one inductive-capacitive (LC) tank. The implantable lead assembly may include a conductor coupled to the LC tank. For example, a portion of the conductor may be wound to form the LC tank. To illustrate, a first section of the conductor may be wound in the first direction. A second section of the conductor may be wound in a second direction to overlap a first portion of the first section. For example, a second portion of the first section may not be overlapped by the second section. The second direction may be opposite the first direction. A third section of the conductor may be wound in the first direction to overlap the second section. A remaining portion of the conductor may be wound in the first direction. The LC tank may include the overlapping sections (e.g., the first portion of the first section, the second section, and the third section). In a particular embodiment, the implantable lead assembly may exclude the second portion of the first section and the remaining portion. For example, the entire length of the conductor may form the LC tank.

The LC tank may be formed (e.g., tuned) so that the impedance of the implantable lead assembly satisfies an impedance threshold (e.g., approximately 1 kilo-ohm (kOhm)) for an electro-magnetic field that has a frequency corresponding to a typical MRI frequency. For example, the electro-magnetic field may induce a current in the implantable lead assembly. The induced current may have a frequency corresponding to the frequency of the electro-magnetic field. For example, the induced current may have the same frequency as the electro-magnetic field. The impedance of the implantable lead assembly may be greater than or equal to the impedance threshold when a current induced by an external electro-magnetic field has a first frequency (e.g., approximately 64 megahertz (MHz) or a second frequency (e.g., approximately 124 MHz). For example, the impedance of the implantable lead assembly may be greater than or equal to the impedance threshold when the external electro-magnetic field has the first frequency (e.g., approximately 64 megahertz (MHz) corresponding to a 1.5 Tesla (T) MRI system), and may be greater than or equal to the impedance threshold when the external electro-magnetic field has the second frequency (e.g., approximately 124 MHz corresponding to a 3 T MRI device).

The impedance of the implantable lead assembly may have a peak impedance for an electro-magnetic field having a third frequency (e.g., a frequency greater than or equal to 90 MHz and less than or equal to 102 MHz). The third frequency may be between the first frequency and the second frequency. The impedance of the implantable lead assembly may generally increase from a first impedance value corresponding to the first frequency to the peak impedance corresponding to the third frequency. The impedance of the implantable lead assembly may generally decrease from the peak impedance to a second impedance value corresponding to the second frequency. The first impedance value and the second impedance value may be greater than or equal to the impedance threshold (e.g., approximately 1 kOhm).

The impedance of the implantable lead assembly may have impedance values that are below the impedance threshold for a current having a frequency that is below the first frequency or greater than the second frequency. For example, a current having a frequency that is below the first frequency (or greater than the second frequency) may be generated in the implantable lead assembly by a pulse generator, e.g., to provide therapy to the patient.

The impedance threshold may be selected such that when exposed to the external electro-magnetic field at the first frequency or at the second frequency, the implantable lead assembly is able to safely dissipate the induced current without significant (e.g., greater than 2 degrees Celsius) localized heating. For example, the impedance threshold may be about 1 kOhm. Thus, in this example, the implantable lead assembly may have an impedance of about 1 kOhm with respect to a current induced by a 1.5 T MRI system and may have an impedance of about 1 kOhm with respect to a current induced by a 3 T MRI system. Accordingly, a patient with the implantable lead assembly may safely undergo a 1.5 T MRI procedure or a 3 T MRI procedure without removing the implantable lead assembly.

According to another particular embodiment, the system may include an implantable lead assembly and a medical device. The implantable lead assembly may include a first connector, a second connector, and a first conductor connecting the first connector and the second connector. The first connector may couple the medical device to the implantable lead assembly, and the second connector may be coupled to an electrode that may be placed on and/or implanted within a patient's body.

The medical device may include a header and a housing. In certain cases, the housing may be used to house a pulse generator. The pulse generator may be configured to generate a stimulation signal and to provide the stimulation signal to tissue of the patient via the implantable lead assembly. In addition, the medical device may include a filter, such as a band-stop filter. The filter may be included within the header or the housing of the medical device. Furthermore, the filter may be configured such that a combined impedance of the filter and the implantable lead assembly may be tuned based on a current induced by an external electro-magnetic field caused by an MRI procedure.

The induced current may have a frequency corresponding to the frequency of the electro-magnetic field (e.g., the induced current may have the same frequency as the electro-magnetic field). As such, the filter may be configured such that the combined impedance of the filter and the implantable lead assembly may be greater than or equal to an impedance threshold when the induced current has a first frequency (e.g., approximately 64 MHz) and/or a second frequency (e.g., approximately 124 MHz). For example, the combined impedance may be greater than or equal to the impedance threshold when the external electro-magnetic field has the first frequency (e.g., approximately 64 MHz corresponding to a 1.5 T MRI system). The combined impedance may also be greater than or equal to the impedance threshold when the external electro-magnetic field has the second frequency (e.g., approximately 124 MHz corresponding to a 3 T MRI device).

Moreover, the filter may be configured such that the combined impedance may have a peak impedance for an electro-magnetic field having a third frequency (e.g., a frequency greater than or equal to 90 MHz and less than or equal to 102 MHz). The third frequency may be between the first frequency and the second frequency. The combined impedance of the filter and the implantable lead assembly may generally increase from a first impedance value corresponding to the first frequency to the peak impedance corresponding to the third frequency. The combined impedance of the filter and the implantable lead assembly may generally decrease from the peak impedance to a second impedance value corresponding to the second frequency. The first impedance value and the second impedance value may be greater than or equal to the impedance threshold (e.g., approximately 1 kOhm). Thus, the combined impedance may satisfy the impedance threshold continuously for the entire frequency range between the first frequency and the second frequency.

Further still, the combined impedance may correspond to impedance values that are below the impedance threshold for an induced current (e.g., or the corresponding electro-magnetic field) having a frequency that is below the first frequency or greater than the second frequency. For example, an induced current having a frequency that is below the first frequency (or greater than the second frequency) may be generated in the implantable lead assembly by a pulse generator, e.g., to provide therapy to the patient.

The impedance threshold may be selected such that when exposed to the external electro-magnetic field at the first frequency or at the second frequency (e.g., or any frequency between the first frequency and the second frequency), the medical device system is able to safely dissipate the induced current in the implantable lead assembly without significant (e.g., greater than 2 degrees Celsius) localized heating. For example, the impedance threshold may be about 1 kOhm. Thus, in this example, the filter and the implantable lead assembly may have a combined impedance of about 1 kOhm with respect to a current induced by a 1.5 T MRI system and may have a combined impedance of about 1 kOhm with respect to a current induced by a 3 T MRI system. Accordingly, a patient using the medical device system may safely undergo a 1.5 T MRI procedure or a 3 T MRI procedure without removing the implantable lead assembly and/or other components of the medical device system.

Additionally or in the alternative, a tuning circuit may also be coupled to the filter. The tuning circuit may be configured to receive a tuning signal, and based on the tuning signal, the tuning circuit may be configured to adjust the combined impedance of the filter and the implantable lead assembly. For example, the combined impedance may be adjusted such that the impedance threshold is satisfied when the electro-magnetic field has a fourth frequency. The fourth frequency may be outside of the frequency range between the first frequency and the second frequency (e.g., the fourth frequency may be less than the first frequency or greater than the second frequency). The tuning circuit may be configured to adjust the combined impedance of the filter and the implantable lead assembly to satisfy the impedance threshold at any desired frequency of the induced current and/or the electro-magnetic field.

In another particular embodiment, an implantable lead assembly includes a first conductor and at least one inductive-capacitive (LC) tank coupled to the first conductor. The first conductor is configured to be coupled to a medical device. An impedance of the implantable lead assembly with respect to a current induced by an external electro-magnetic field satisfies an impedance threshold when the external electro-magnetic field has a first frequency, satisfies the impedance threshold when the external electro-magnetic field has a second frequency, and has a peak impedance value when the external electro-magnetic field has a third frequency that is between the first frequency and the second frequency.

In another particular embodiment, a system includes a pulse generator and an implantable lead assembly. The implantable lead assembly includes a conductor configured to be coupled to the pulse generator. At least one inductive-capacitive (LC) tank is coupled to the first conductor. An impedance of the implantable lead assembly with respect to a current induced by an external electro-magnetic field satisfies an impedance threshold when the external electro-magnetic field has a first frequency, satisfies the impedance threshold when the external electro-magnetic field has a second frequency, and has a peak impedance value when the external electro-magnetic field has a third frequency that is between the first frequency and the second frequency In another particular embodiment, a lead assembly includes a coiled first length of wire forming a first section of a coiled conductor. The lead assembly also includes a coiled second length of the wire corresponding to at least one LC tank. The at least one LC tank includes a plurality of overlapping windings of the wire. The coiled conductor is formed by coiling the wire along an axis in a first direction. The LC tank is formed by coiling a first portion of the wire in a second direction opposite the first direction to form a first overlapping winding on a portion of the coiled conductor, and by coiling a second portion of the wire in the first direction to form a second overlapping winding on the first overlapping winding. The LC tank may include an insulation layer between adjacent windings.

One particular advantage provided by at least one of the disclosed embodiments is that a patient with an implantable lead assembly may safely undergo a 1.5 T MRI procedure or a 3 T MRI procedure without removing the implantable lead assembly. For example, the implantable lead assembly may have an impedance of about 1 kOhm with respect to a current induced by a 1.5 T MRI system and may have an impedance of about 1 kOhm with respect to a current induced by a 3 T MRI system. At an impedance of about 1 kOhm, the implantable lead assembly may safely dissipate the induced current without significant (e.g., greater than 2 degrees Celsius) localized heating.

The features, functions, and advantages that have been described can be achieved independently in various embodiments or may be combined in yet other embodiments, further details of which are disclosed with reference to the following description and drawings.

DETAILED DESCRIPTION

Figure 1:
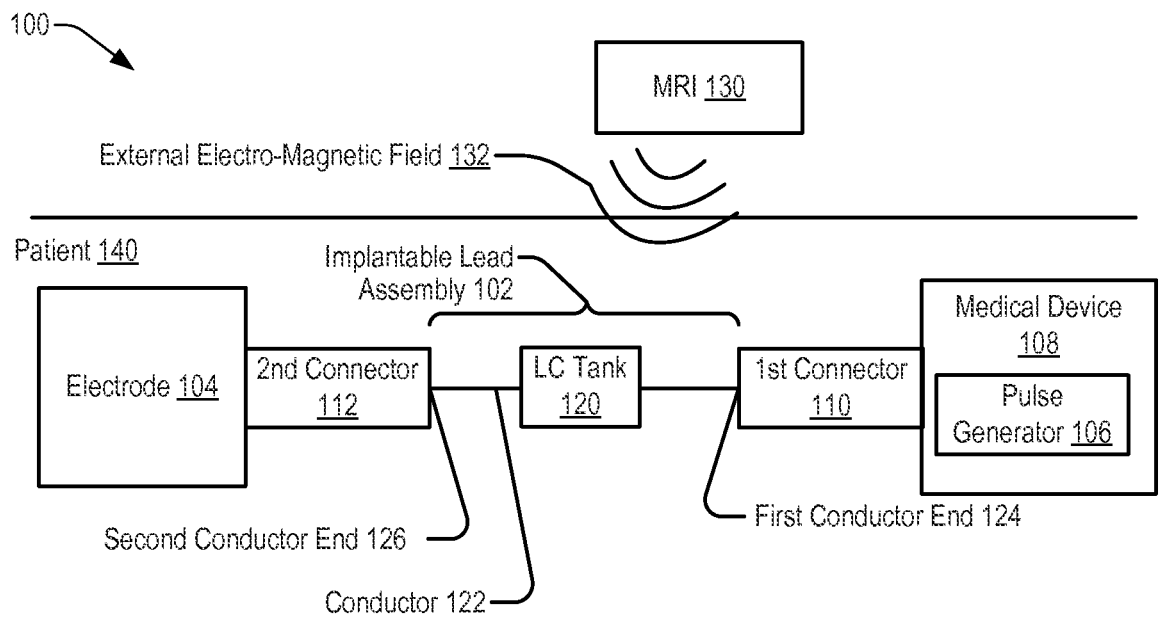
FIG. 1 is a block diagram of a particular embodiment of a system that uses an implantable lead assembly.

Referring to FIG. 1, a system 100 including an implantable lead assembly 102 is shown. The implantable lead assembly 102 may be coupled, via a first connector 110, to a medical device 108 and may be coupled, via a second connector 112, to an electrode 104. The implantable lead assembly 102 may include a conductor 122 extending from a first conductor end 124 to a second conductor end 126. The first conductor end 124 may be coupled, via the first connector 110, to the pulse generator 106. The second conductor end 126 may be coupled, via the second connector 112, to the electrode 104.

In a particular embodiment, the system 100, or a portion thereof, may be implanted within tissue of a patient 140 to provide therapy or to sense information from the tissue of the patient 140. For example, the electrode 104 may be configured to sense information related to tissue of a patient 140 (e.g., electrical signals generated by a nerve of the patient 140) and to provide the information to the medical device 108 via the implantable lead assembly 102. In another example, the electrode 104 may be configured to apply an electrical signal from the medical device 108 to the tissue of the patient 140. To illustrate, the medical device 108 may include a pulse generator 106, which may generate stimulation signals that can be applied to the tissue of the patient 140, via the implantable lead assembly 102 and the electrode 104, to treat a medical condition of the patient 140. Exemplary medical conditions that may be treated include a medical disorder, a psychiatric disorder, a physiological disorder, an involuntary movement disorder, a seizure disorder, a sleep disorder (e.g., apnea or insomnia), depression, a heart disorder, a neurological disorder, a neuro-muscular disorder, a bladder disorder, and obesity.

After the system 100, or a portion of the system 100 (such as the electrode 104 and at least a portion of the implantable lead assembly 102), is implanted within tissue of the patient 140, removing the system 100 may require a surgical procedure. To avoid removing the system 100 from the patient 140 while the patient 140 undergoes a magnetic resonance imaging (MRI) procedure, the implantable lead assembly 102 may be designed to be MRI safe or MRI resistant. The implantable lead assembly 102 may be configured to safely dissipate currents induced in the implantable lead assembly 102 by an external electro-magnetic field 132 of an MRI system 130.

The implantable lead assembly 102 may be exposed to the external electro-magnetic field 132 during a magnetic resonance imaging (MRI) procedure of the patient 140. An impedance of the implantable lead assembly 102 may be based on a current induced within the lead assembly 102 or a component thereof by the external electro-magnetic field 132. For example, the impedance of the implantable lead assembly 102 may be based on a frequency of the induced current. The induced current may have the same frequency as the external electro-magnetic field 132. The impedance of the implantable lead assembly 102 may satisfy (e.g., may be greater than or equal to) an impedance threshold (e.g., approximately 1 kOhm) when the external electro-magnetic field 132 has a first frequency (e.g., approximately 64 megahertz (MHz)) and when the external electro-magnetic field has a second frequency (e.g., approximately 128 MHz). The first frequency may correspond to a 1.5 T MRI system. The second frequency may correspond to a 3 T MRI system. The impedance threshold (e.g., approximately 1 kOhm, or greater than or equal to 0.9 kilo-ohm (kOhm) and less than or equal to 1.1 kOhm) may include a range of impedance values.

The impedance threshold may be selected such that when exposed to the external electro-magnetic field 132 having the first frequency or having the second frequency, the implantable lead assembly 102 is able to safely dissipate the induced current without significant (e.g., greater than 2 degrees Celsius) localized heating. The implantable lead assembly 102 may be MRI-compliant (e.g., magnetic resonance (MR) safe, MR compatible, or both) for an MRI procedure that uses the first frequency and/or for an MRI procedure that uses the second frequency.

The implantable lead assembly 102 may have a peak impedance value (e.g., an anti-resonance value) when the external electro-magnetic field 132 has a third frequency (e.g., a frequency greater than or equal to approximately 90 MHz and less than or equal to approximately 102 MHz), as further described with reference to FIG. 4. The third frequency may be higher than the first frequency and lower than the second frequency. The implantable lead assembly 102 may include at least one inductive-capacitive (LC) tank (e.g., an LC tank 120) configured to provide the implantable lead assembly 102 specific impedance values when the assembly 102 is exposed to 1.5 T and/or 3.0 T magnetic fields.

The LC tank 120 may be coupled to the conductor 122. The LC tank 120 may be formed by winding the conductor 122 (e.g., as further described with reference to FIGS. 5-14). The winding configuration may be selected to provide the implantable lead assembly 102 the specific impedance values desired when the assembly 102 is exposed to 1.5 T and/or 3.0 T magnetic fields. For example, a first section of the conductor 122 may be wound in a first direction (e.g., forward or distally). A second section of the conductor 122 may be wound in a second direction (e.g., backward or proximally) to overlap at least a portion of the first section. The second direction may be opposite of the first direction. A third section of the conductor 122 may be wound in the first direction to overlap at least a portion of the second section there by providing a layering or overlapping of the conductor 122 over itself to form the LC tank 120. The LC tank 120 may include the overlapping sections (e.g., the first section, the second section, and the third section) of the conductor 122. In a particular embodiment, the conductor 122 may be wound to form a single LC tank (e.g., the LC tank 120). In an alternate embodiment, multiple LC tanks may be coupled to the conductor 122. For example, the LC tank 120 may be coupled to a second LC tank by a portion of the conductor 122.

The LC tank 120 (e.g., formed as described with reference to FIGS. 5-14) may be configured to provide an impedance characteristic or value (or, stated another way, tuned to provide an impedance characteristic or value) of the implantable lead assembly 102 so that the impedance satisfies the impedance threshold when the external electro-magnetic field 132 has a first frequency (e.g., approximately 64 MHz), satisfies the impedance threshold when the external electro-magnetic field 132 has a second frequency (e.g., approximately 128 MHz), and has a peak impedance value when the external electro-magnetic field 132 has a third frequency (e.g., greater than or equal to 90 MHz and less than or equal to 102 MHz).

The LC tank 120 may include multiple conductive elements, such as described with reference to FIGS. 5-14 that either alone or in combination with the remainder of the conductor 122 windings provide a desired impedance characteristic or value for 1.5 T and/or 3.0 T magnetic fields. For example, the LC tank 120 may include overlapping windings of the conductor 122. The LC tank 120 may include conductive elements arranged to form a cavity, e.g., as described with reference to FIG. 13. The cavity may include a core (e.g., an air core, a metallic core, or a non-metallic core). For example, a core insert may be disposed in the cavity. The core insert may be metallic or non-metallic. The core insert may include at least one of iron, silver, platinum, gold, tungsten, or iridium. The core insert may include a metal alloy including at least one of iron, silver, platinum, gold, tungsten, or iridium. The core insert may include iron-platinum (Fe—Pt) pellets.

The implantable lead assembly 102 may direct electrical energy to an LC tank (e.g., the LC tank 120). For example, the implantable lead assembly 102 may orient the electrical energy about a core (e.g., a core insert) of the LC tank 120. The electrical energy may be generated by the external electro-magnetic field 132. For example, the electrical energy may be generated by a current induced in the implantable lead assembly 102 by the external electro-magnetic field 132. The LC tank 120 may dampen the electrical energy so as to limit a temperature increase of the implantable lead assembly 102, the electrode 104, tissue in which the electrode 104 is implanted, or a combination thereof, to within a particular temperature (e.g., two degrees Fahrenheit or two degrees Celsius). For example, the LC tank 120 may dissipate at least a portion of the electrical energy to limit the temperature increase when the external electro-magnetic field 132 applied by an MRI system 130 has a first frequency (e.g., approximately 64 MHz) or has a second frequency (e.g., approximately 128 MHz).

The impedance of the implantable lead assembly 102 may be based on a capacitance of the implantable lead assembly 102, an inductance of the implantable lead assembly 102, a frequency of the external electro-magnetic field 132, or a combination thereof. The inductance of the implantable lead assembly 102 may be based on inductance from coiling of a conductor (e.g., the conductor 122) along the implantable lead assembly 102 including an inductance of one or more LC tanks coupled to the conductor. For example, the impedance of the implantable lead assembly 102 may be based on inductance from coiling of the conductor 122 along the implantable lead assembly 102.

The inductance from the coiling may also be provided by variations in wire material of the conductor 122, a structure (e.g., a silver core) of the wire of the conductor 122, a diameter of the wire of the conductor 122, a diameter of a coil of the conductor 122, a pitch of the coil of the conductor 122, a density of the coil of the conductor 122, a spacing between adjacent coils of the conductor 122, quality of insulation between adjacent coils of the conductor 122, or a combination thereof.

The inductance of the implantable lead assembly 102 may be provided by the inductance characteristics arising from the overlapping of a conductor (e.g., the conductor 122) to form an LC tank (e.g., the LC tank 120). The inductance from overlapping may be based on variations in overlapping (e.g., winding) technique, such as winding techniques described with reference to FIGS. 5-14. The inductance from overlapping may be based on a length of an overlap, a length of the LC tank 120, a diameter of a coil (e.g., an inner coil, an outer coil, or both) of the LC tank 120, a degree of symmetry of the LC tank 120, or a combination thereof.

The inductance of the implantable lead assembly 102 may be provided by the inductance attributable to a core of an LC tank (e.g., a core of the LC tank 120). The inductance from the core may be based on whether the core (e.g., a cavity formed by one or more coils) includes air, whether the core includes a core insert, material properties (e.g., metallic or non-metallic) of the core insert, or a combination thereof.

The capacitance of the implantable lead assembly 102 may be provided by a capacitance (e.g., a parasitic capacitance) arising between adjacent portions of coils or from individual coils (e.g., a loop or a series of loops adjacent or near to another loop or another series of loops). The coils, series of coils, or portions of the coils may be horizontally, vertically, or diagonally adjacent to each other. For example, a first coil may be between a second coil and a third coil along a particular axis (e.g., a horizontal axis, a vertical axis, or a diagonal axis). A portion of the first coil may be adjacent to a portion of the second coil. A portion of the first coil may be adjacent to a portion of the third coil. The capacitance of the implantable lead assembly 102 may be provided by a parasitic capacitance observed between adjacent portions of the first coil and the second coil and between adjacent portions of the first coil and the third coil.

The capacitance of the implantable lead assembly 102 may be provided by a length of a conductor (e.g., the conductor 122), a number of coils of the conductor 122, a density of the coils of the conductor 122, a spacing between the coils of the conductor 122, an insulation material disposed between the coils of the conductor 122, or a combination thereof. The capacitance of the implantable lead assembly 102 may be provided by one or more material properties of a wire of a conductor (e.g., the conductor 122), a dielectric strength of the conductor 122, or a combination thereof.

The LC tank 120 may be approximately equidistant from the first conductor end 124 and the second conductor end 126, as illustrated in FIG. 1. In another embodiment, the LC tank 120 may be proximate to the first conductor end 124 or proximate to the second conductor end 126. In a particular embodiment, the LC tank 120 may extend from the first conductor end 124 to the second conductor end 126.

In a particular embodiment, at least one LC tank (e.g., the LC tank 120) may be proximate to (e.g., included in or included partially in) the medical device 108, the first connector 110, the second connector 112, the pulse generator 106, a battery of the system 100, a hermetically sealed portion of the pulse generator 106, a hermetically sealed portion of the medical device 108, or another location of the system 100. The LC tank (e.g., the LC tank 120) may operate regardless of whether the pulse generator 106 is activated (e.g., powered). In a particular embodiment, at least one LC tank (e.g., the LC tank 120) may be proximate to (e.g., included in or a portion of) the electrode 104 (e.g., a nerve cuff electrode). In this embodiment, a heat sink may be proximate to the LC tank (e.g., the LC tank 120). In a particular embodiment, at least one LC tank (e.g., the LC tank 120) may be external to the medical device 108, the first connector 110, the second connector 112, the pulse generator 106, a battery of the system 100, or a combination thereof. For example, as illustrated in FIG. 1, the LC tank 120 may be external to the first connector 110, the second connector 112, the medical device 108, and the pulse generator 106.

A coiled implantable lead assembly 102 that includes an LC tank (e.g., the LC tank 120) may have approximately the same length (e.g., 17 inches) as a coiled implantable lead assembly 102 excluding the LC tank. For example, the LC tank 120 may add little or no length to the implantable lead assembly 102 when the implantable lead assembly 102 is coiled. As can be appreciated, the length of the conductor forming the lead of the lead assembly 102 and the LC tank portion of the lead assembly 102 may have a conductor length defined to extend from one point to another point along the length of the conductor as the conductor forms the loops of the lead assembly 102, with the conductor length following the length of each loop of the wound conductor. As can also be appreciated the conductor length can be defined by the overall axial length of the wound lead assembly or LC tank with the contribution of each looped length disregarded and with each loop contributing an axial length defining each loops contribution to the axial length of the assembly 102, with that loop axial length being similar to the thickness of the conductor wire.

An uncoiled implantable lead assembly 102 that includes an LC tank (e.g., the LC tank 120) may be longer than an uncoiled implantable lead assembly 102 that excludes the LC tank, which can be due to the extra windings and doubling-back configuration of the conductor that may be used to form the LC tank along the length of the conductor. For example, the LC tank 120 may add length to the implantable lead assembly 102 when the implantable lead assembly 102 is uncoiled (or stretched). To illustrate, the implantable lead assembly 102 including the LC tank 120 may have a first length (e.g., approximately 400 inches) when the implantable lead assembly 102 is uncoiled (e.g., stretched). The implantable lead assembly 102 excluding the LC tank 120 may have a second length (e.g., approximately 80 inches) when the implantable lead assembly 102 is uncoiled. The first length may be greater (e.g., more than twice) the second length. The uncoiled implantable lead assembly 102, with or without the LC tank, may have a greater length (e.g., approximately 80 inches or approximately 400) than a length (e.g., approximately 17 inches) of the coiled implantable lead assembly 102.

The pulse generator 106 may provide electrical stimulation via the electrode 104 to tissue of the patient 140. For example, the pulse generator 106 may apply a signal, via the implantable lead assembly 102, to tissue of the patient 140. The signal may generate a current in the implantable lead assembly 102. An impedance of the implantable lead assembly 102 may be based on the current. For example, the impedance of the implantable lead assembly 102 may be based on a frequency of the current. The impedance of implantable lead assembly 102 may fail to satisfy the impedance threshold when the signal is applied to the implantable lead assembly 102. For example, the frequency of the current may be lower than a first frequency (e.g., approximately 64 MHz) or greater than a second frequency (e.g., approximately 128 MHz). The impedance of the implantable lead assembly 102 may be lower than the impedance threshold when the signal is applied by the pulse generator 106. For example, the impedance of the implantable lead assembly 102 may have an impedance value that is lower than the impedance threshold when a frequency of the current is lower than the first frequency or when the frequency of the current is greater than the second frequency. The lower impedance value may enable the signal to reach (e.g., provide electrical stimulation to) the tissue of the patient 140.

Figure 2:
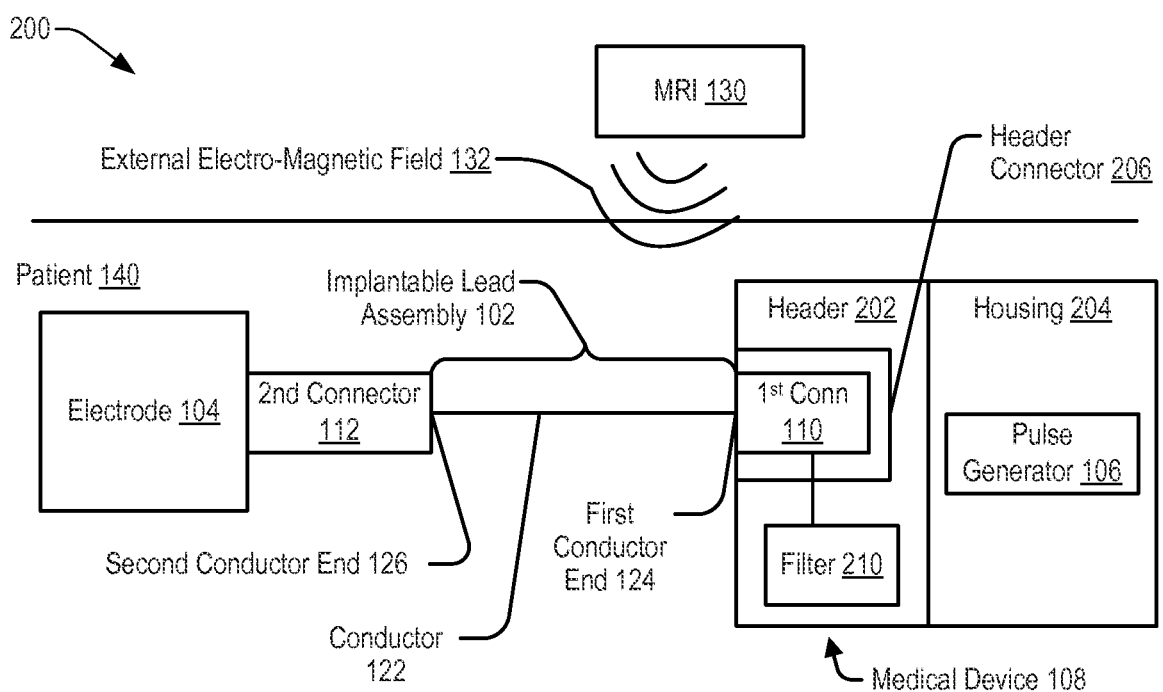
FIG. 2 is a block diagram of another particular embodiment of a system that uses an implantable lead assembly and a filter.

FIG. 2 illustrates a diagram of a system 200 according to another particular embodiment. The system 200 may include one or more components that are similar and/or that otherwise correspond to components of the system 100 illustrated in FIG. 1. To this end, like numbers indicate like parts with respect to FIG. 1 and FIG. 2. The system 200 may include a medical device 108, and the medical device 108 may include a header 202 and a housing 204. The housing 204 may house and/or otherwise include the pulse generator 106. The header 202 may include a header connector 206 to connect to the first connector 110 of the implantable lead assembly 102. Additionally or in the alternative, the header 202 may include both the header connector 206 and the first connector 110 when the implantable lead assembly 102 is coupled to the medical device 108. The header 202 may also include a filter 210, which may be coupled to the implantable lead assembly 102, such as via the first connector 110. In certain embodiments, the filter 210 may be a band-stop filter that may be configured to attenuate signals at particular frequencies and/or particular frequency ranges. Additionally, though FIG. 2 depicts the filter 210 as being included within the header 202, in other examples the filter 210 may be included within other parts of the medical device 108 as well, such as the housing 204 and/or a feed-through area (not pictured) located between the header 202 and the housing 204. In addition, the filter 210 may also be a component that is interposed between the first connector 110 and the header 202, and may be configured to be an interface or an adapter providing a connection between the conductor 112 and the header 202

The filter 210 may include one or more LC circuits and/or LCR circuits. For instance, the filter may include an LC tank, such as LC tank 120. As previously discussed, the inductance of the LC tank may be provided by variations in overlapping (e.g., winding) technique of a conductor, such as winding techniques described with reference to FIGS. 5-14. The inductance from overlapping may be provided by a length of an overlap, a length of the LC tank 120, a diameter of a coil (e.g., an inner coil, an outer coil, or both) of the LC tank 120, a degree of symmetry of the LC tank 120, or a combination thereof. Further, the capacitance of the LC tank 120 may be provided by a capacitance (e.g., a parasitic capacitance) between adjacent portions of coils formed by the windings. Additionally or in the alternative, the filter 210 may include discrete inductor and/or capacitor components to form the LC and/or LCR circuits. For instance, the inductance of an LC circuit in the filter 210 may be provided by a discrete inductor or inductors, and the capacitance of the LC circuit may be provided by a discrete capacitor or capacitors, rather than relying on a parasitic capacitance such as in the LC tank 120. In an LCR circuit, the resistance or damping effect may be provided by a discrete resistor or resistors. In other examples, the LC and/or LCR components (e.g., the inductor(s), capacitor(s), and/or resistor(s)) may be formed within an integrated circuit. Moreover, the impedance of the filter 210 may adjustable via a tuning circuit, which may be described in more detail below with reference to FIG. 3.

As previously discussed, the implantable lead assembly 102 may be exposed to the external electro-magnetic field 132 during a MRI procedure of the patient 140. The electro-magnetic field 132 may induce a current in the implantable lead assembly 102 or a component thereof, and in certain implementations, both the electro-magnetic field 132 and the induced current may have the same or approximately the same frequency. As such, the filter 210 may be configured such that a combined impedance of the filter 210 and the implantable lead assembly 102 may satisfy an impedance threshold when the electro-magnetic field 132 has a particular frequency and/or has particular frequency within a certain frequency range.

For instance, the combined impedance of the filter 210 and the implantable lead assembly 102 may satisfy (e.g., may be greater than or equal to) an impedance threshold (e.g., approximately 1 kOhm) when the external electro-magnetic field 132 has a first frequency (e.g., approximately 64 megahertz (MHz)) and when the external electro-magnetic field has a second frequency (e.g., approximately 128 MHz). The first frequency may correspond to a 1.5 T MRI system. The second frequency may correspond to a 3 T MRI system. The impedance threshold (e.g., approximately 1 kOhm, or greater than or equal to 0.9 kilo-ohm (kOhm) and less than or equal to 1.1 kOhm) may include a range of impedance values.

Further still, the combined impedance may correspond to impedance values that are below the impedance threshold for an induced current (e.g., or the corresponding electro-magnetic field 132) having a frequency that is below the first frequency or greater than the second frequency. For example, an induced current having a frequency that is below the first frequency (or greater than the second frequency) may be generated in the implantable lead assembly by the pulse generator 106, e.g., to provide therapy to the patient. Thus, stimulation signals provided by the pulse generator 106 may be able to bypass the filter 210. Additionally or in the alternative, the filter 210 may be disabled (e.g., by a tuning circuit described in more detail below) while the pulse generator 106 generates and/or transmits stimulation signals.

The impedance threshold may be selected such that when exposed to the external electro-magnetic field 132 having the first frequency or having the second frequency, the filter 210 is able to safely dissipate the induced current in the implantable lead assembly 102 without significant (e.g., greater than 2 degrees Celsius) localized heating. As a result, the implantable lead assembly 102 may be MRI-compliant (e.g., magnetic resonance (MR) safe, MR compatible, or both) for an MRI procedure that uses the first frequency and for an MRI procedure that uses the second frequency.

Furthermore, the combined impedance of the filter 210 and the implantable lead assembly 102 may correspond to a peak impedance value (e.g., an anti-resonance value) when the external electro-magnetic field 132 has a third frequency (e.g., a frequency greater than or equal to approximately 90 MHz and less than or equal to approximately 102 MHz), as further described with reference to FIG. 4. The third frequency may be greater than the first frequency and less than the second frequency.

Figure 3:
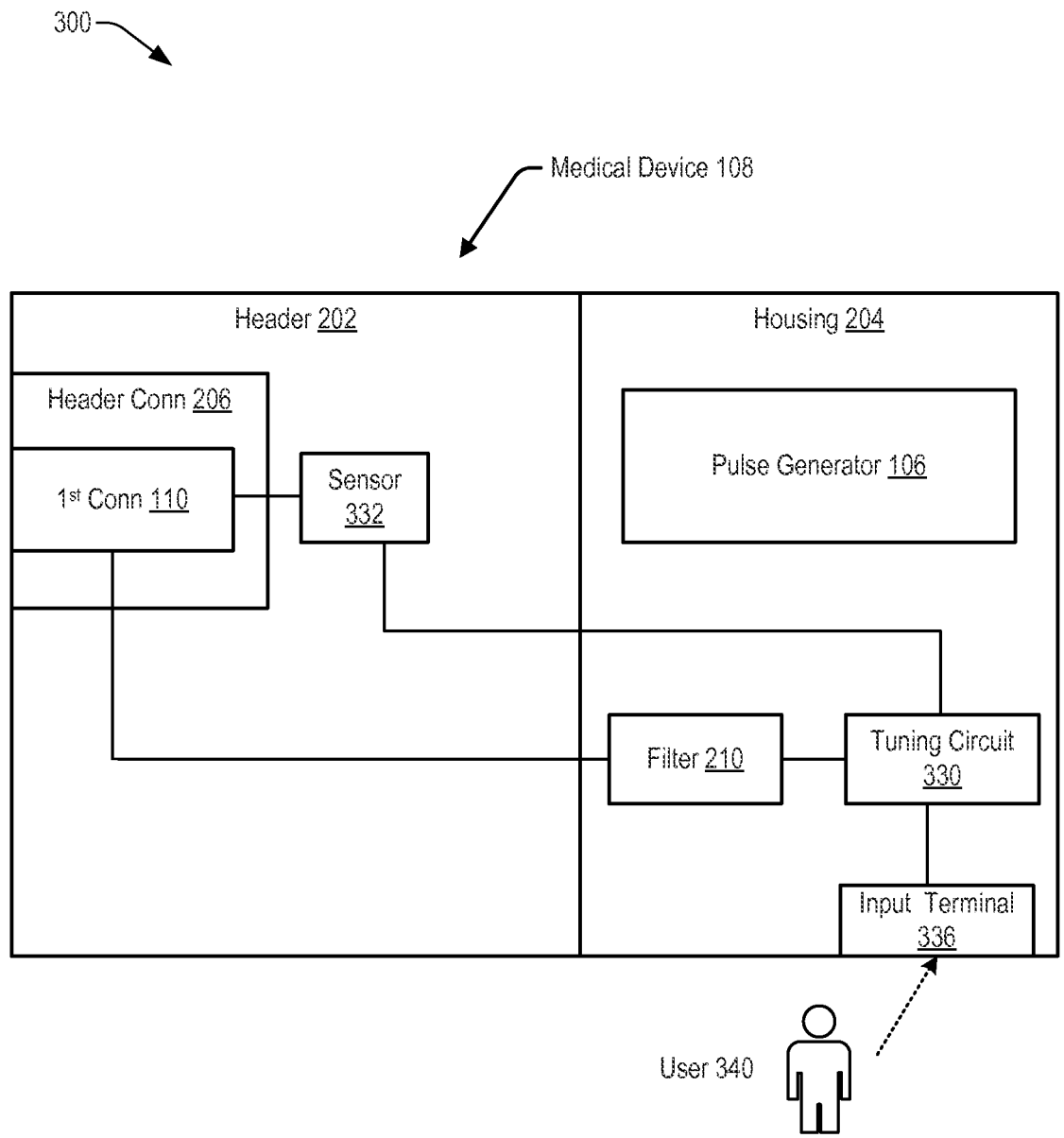
FIG. 3 is a block diagram of another particular embodiment of a medical device that uses an implantable lead assembly and a filter.

Referring now to FIG. 3, a system 300 is illustrated of a medical device 108 that includes a tuning circuit 330. The tuning circuit 330 may be coupled to the filter 210. The tuning circuit 330 may be configured to receive a tuning signal and adjust, based on the tuning signal, the combined impedance of the filter 210 and the implantable lead assembly 102 to satisfy the impedance threshold at different frequencies. For instance, continuing with the previous example, the tuning circuit 330 may adjust the combined impedance to satisfy the impedance threshold at a fourth frequency, where the fourth frequency may be outside of the frequency range between the first frequency and the second frequency. For example, the fourth frequency may be less than the first frequency or greater than the second frequency.

In other examples, the tuning circuit 330 may be configured to disable the filter 210 and/or enable bypass of the filter 210. For instance, the tuning circuit 330 may act as a switch for the filter 210 and may disable the filter 210, such as when stimulation signals are generated by the pulse generator 106. In yet other examples, the tuning circuit 330 may also be configured to adjust the combined impedance of the implantable lead assembly 102 and the filter 210 according to particular MRI procedures and/or MRI systems. For instance, the tuning circuit 330 may adjust the combined impedance to satisfy a different impedance threshold at different frequencies for a 1.5 T MRI system than for a 3.0 T MRI system.

The tuning circuit 330 may be configured to receive the tuning signal in response to various indications, such as from a user 340 via a wired or wireless programming signal or a sensor 332 coupled to the implantable lead assembly 102 (e.g., via the first connector 110). For instance, the tuning circuit 330 may be configured to measure an energy value, such as via the sensor 332, associated with the implantable lead assembly 102. In certain implementations, the energy value may correspond to a temperature of the implantable lead assembly 102. As such, the tuning circuit 330 may receive the tuning signal in response to the energy value satisfying an energy threshold. For instance, the sensor 332 may detect that the temperature of the implantable lead assembly 102 is greater than or equal to a particular temperature threshold and provide a corresponding indication to the tuning circuit 330. Additionally or in the alternative, the sensor 332 may be configured to provide periodic energy value (e.g., temperature) measurements to the tuning circuit 330, and the tuning circuit 330 may perform a determination as to whether the energy value satisfies the energy threshold.

According to another particular embodiment, the tuning circuit 330 may receive the tuning signal in response to a discrete input, such as via an input terminal 336, from a user 340 of the medical device 108. For example, the user 340 may be a medical professional that may wish to tune the filter 210 in order to ensure operational safety of the system 200 during an MRI procedure performed by a particular MRI machine 130. The medical professional may program the filter 210 by providing one or more inputs via the input terminal 336. As a result of the input(s), a tuning signal may be transmitted to the tuning circuit 330. In response to receiving the tuning signal, the tuning circuit 330 may adjust the filter 210 accordingly (e.g., the combined impedance of the filter 210 and the implantable lead assembly 102 may be adjusted to satisfy an impedance threshold when the electro-magnetic field 132 reaches a particular frequency or particular frequencies).

The systems 100, 200, and 300 may enable a safe MRI procedure to be performed using the implantable lead assembly 102. For example, an impedance of the implantable lead assembly 102 and/or a combined impedance of the implantable lead assembly 102 and the filter 210 may satisfy an impedance threshold when the implantable lead assembly 102 is exposed to the external electro-magnetic field 132 having a first frequency during an MRI procedure.

In addition, the systems 100, 200, and 300 may enable a single lead assembly to be used to perform MRI procedures having various frequencies. For example, the implantable lead assembly 102 may be used to perform a first MRI procedure using an external electro-magnetic field having a first frequency or to perform a second MRI procedure using an external electro-magnetic field having a second frequency. The first frequency may correspond to a 1.5 T MRI system and the second frequency may correspond to a 3 T MRI system. A medical professional may thus implant a lead assembly (e.g., the implantable lead assembly 102) in the patient 140 prior to determining whether the patient 140 is to undergo the first MRI procedure or the second MRI procedure.

Furthermore, the medical professional may implant a single lead assembly (e.g., the implantable lead assembly 102) in a patient who is to undergo both the first MRI procedure and the second MRI procedure. One or more components ((e.g., the implantable lead assembly 102, the medical device 108, or both) of the system 100 and 200 may be labeled as MRI safe for the first frequency and for the second frequency. For example, a surface of a component (e.g., the implantable lead assembly 102 or the medical device 108) may include a label (e.g., a pictorial label, a textual label, or both) indicating that the component is MRI safe for the first frequency, for the second frequency, or for both. The label may indicate that the component is compatible with a 1.5 T MRI system, a 3 T MRI system, or both.

Figure 4:
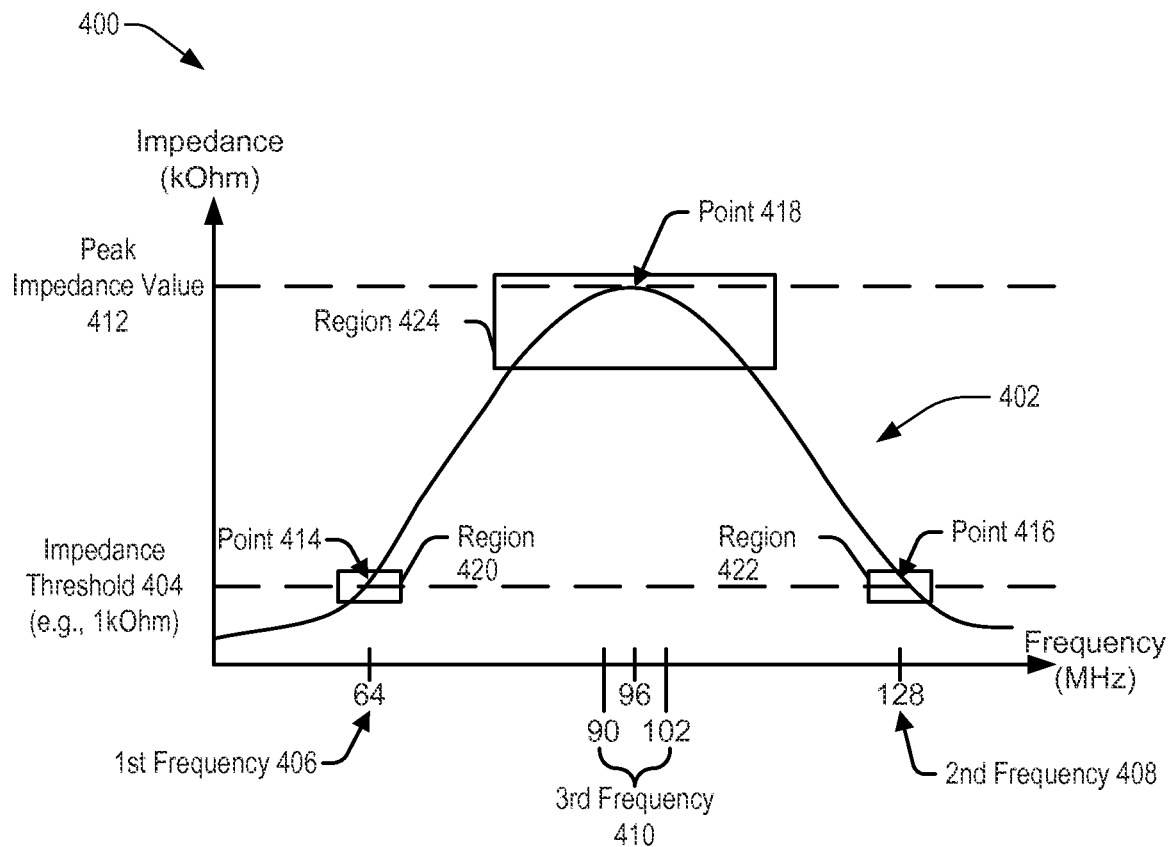
FIG. 4 is a diagram illustrating impedance characteristics of the implantable lead assembly of FIG. 1.

Referring to FIG. 4, a diagram is shown and generally designated at 400. The diagram 400 includes an impedance curve 402. In a particular embodiment, the impedance curve 402 illustrates impedance characteristics of the implantable lead assembly 102 of FIG. 1. In the embodiments of FIGS. 1 and 2, for example, the impedance curve 402 can be based on measured or estimated data or be a representation of the impedance characteristics built into the lead assembly 102, the LC tank 120, and/or components of the assembly 102 by the aforementioned use of specific winding configurations and materials that affect impedance characteristics. For example, the impedance curve 402 may correspond to impedance of the implantable lead assembly 102 relative to frequency of the external electro-magnetic field 132 of FIG. 1. Impedance of the implantable lead assembly 102 may be based on a current induced in the implantable lead assembly 102 by the external electro-magnetic field 132. For example, the impedance may be based on a frequency of the induced current. The frequency of the induced current may be the same as the frequency of the external electro-magnetic field 132.

The diagram 400 includes a region 420, a region 422, and a region 424. The region 420 may correspond to impedance values of the implantable lead assembly 102 when the external electro-magnetic field 132 has a first frequency 406 (e.g., approximately 64 MHz). The first frequency 406 may correspond to a 1.5 T MRI system. Impedance values within the region 420 may satisfy an impedance threshold (e.g., approximately 1 kOhm) when the external electro-magnetic field 132 has the first frequency 406.

The region 422 may correspond to impedance values of the implantable lead assembly 102 when the external electro-magnetic field 132 has a second frequency 408 (e.g., approximately 128 MHz). The second frequency 408 may correspond to a 3 T MRI system. Impedance values within the region 422 may satisfy the impedance threshold (e.g., approximately 1 kOhm) when the external electro-magnetic field 132 has the second frequency 408. The region 424 may correspond to peak impedance values of the implantable lead assembly 102 when the external electro-magnetic field 132 has a third frequency 410 (e.g., greater than or equal to 90 MHz and less than or equal to 102 MHz).

The impedance curve 402 passes through the region 420. For example, the impedance curve 402 includes a point 414 within the region 420. The point 414 indicates a first impedance of the implantable lead assembly 102 when the external electro-magnetic field 132 has the first frequency 406 (e.g., approximately 64 MHz). The point 414, within the region 420, indicates that the first impedance satisfies the impedance threshold (e.g., approximately 1 kOhm).

The impedance curve 402 passes through the region 422. For example, the impedance curve 402 includes a point 416. The point 416 indicates a second impedance of the implantable lead assembly 102 when the external electro-magnetic field 132 has the second frequency 408 (e.g., approximately 128 MHz). The point 416, within the region 422, indicates that the second impedance satisfies the impedance threshold (e.g., approximately 1 kOhm).

The impedance curve 402 passes through the region 424. For example, the impedance curve 402 includes a point 418. The point 418 corresponds to a peak impedance value (e.g., an impedance value 412) of the implantable lead assembly 102 when the external electro-magnetic field 132 has a third frequency 410 (e.g., 96 MHz). For example, the impedance value 412 may be a maximum impedance value for a particular range of frequencies (e.g., greater than or equal to 15 MHz and less than or equal to 150 MHz).

The point 414 (or the point 416) may be determined by measuring the first impedance (or the second impedance) of the implantable lead assembly 102 when the external electro-magnetic field 132 has the first frequency 406 (or the second frequency 408). In a particular embodiment, the point 414, the point 416, the point 418, or a combination thereof, may be estimated based on a plurality of impedance measurements. For example, a plurality of impedance values of the implantable lead assembly 102 corresponding to various frequencies of the external electro-magnetic field 132 may be measured. To illustrate, the implantable lead assembly 102 may include a second conductor coupled to a second electrode attached to the patient 140. The conductor 122, the electrode 104, the second electrode, and the second conductor may form a circuit between the medical device 108 and a region of tissue to which the electrode 104 and the second electrode are attached. The pulse generator 106 may apply a measurement signal having a particular frequency to generate a current in the conductor 122. The measurement signal used to measure the impedance value may have lower amplitude than a therapy signal used to provide therapy to the patient 140 and may have lower amplitude than a current induced during an MRI procedure. The measurement signal may produce little or no electrical energy. The measurement signal may be undetectable by the patient 140.

The medical device 108 may measure an impedance value of the implantable lead assembly 102 corresponding to the particular frequency. For example, the medical device 108 may measure a voltage differential between the conductor 122 and the second conductor. The medical device 108 may determine the impedance value by dividing the voltage differential by the generated current. The medical device 108 may determine a plurality of impedance values corresponding to various frequencies by performing a plurality of impedance measurements. The impedance curve 402, or portions thereof, may be generated by curve fitting the plurality of impedance values.

The impedance curve 402 indicates that the impedance of the implantable lead assembly 102 is lower than the impedance threshold 404 (e.g., less than approximately 1 kOhm) at a therapy frequency (e.g., a frequency below the first frequency 406 or higher than the second frequency 408). The pulse generator 106 of FIG. 1 may apply a signal at the therapy frequency to provide therapy to the patient 140. The lower impedance may enable the signal to reach tissue of the patient 140.

An implantable lead assembly (e.g., the implantable lead assembly 102) having impedance characteristics corresponding approximately to the impedance curve 402 may enable safe MRI procedures to be performed at the first frequency 406 and at the second frequency 408. In addition, the implantable lead assembly 102 may enable therapy to be performed at a frequency (e.g., 5-300 Hz) below the first frequency 406 or at a frequency (e.g., 433 MHz) higher than the second frequency 408. For example, the implantable lead assembly 102 may be used to perform at least one of low-frequency (LF) therapy, high-frequency (e.g., ultra high-frequency (UHF)) therapy, or high-frequency alternating current (HFAC) therapy.

Figure 5:
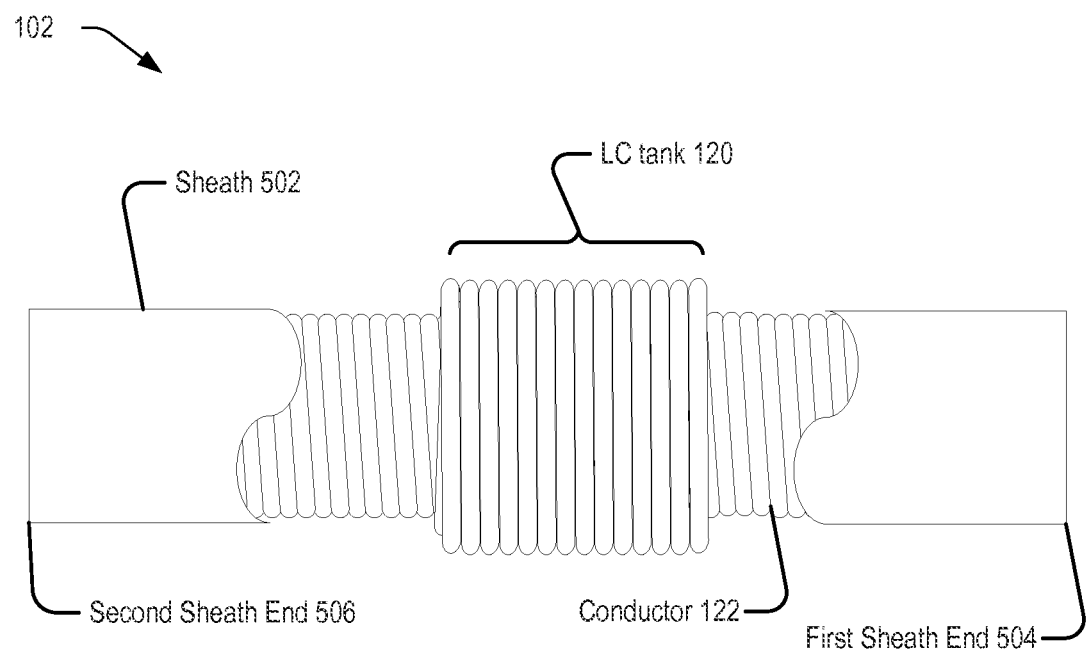
FIG. 5 is a diagram of a particular embodiment of the implantable lead assembly of FIG. 1 having an LC tank and a winding configuration.

Referring to FIG. 5, a diagram of a particular embodiment of the implantable lead assembly 102 is shown. The implantable lead assembly 102 includes a sheath 502 extending from a first sheath end 504 to a second sheath end 506. The sheath 502 may be disposed (e.g., wrapped) over the conductor 122. The conductor 122 may include a nickel cobalt alloy disposed over a silver (Ag) layer, as described with reference to FIG. 14.

The sheath 502 may be disposed on at least a portion of the conductor 122, and the sheath may be an insulator and/or otherwise configured to provide a barrier that provides electrical isolation. The sheath 502 may be disposed over the coiled conductor 122 so as to allow individual adjacent loops of the conductor 122 to electrically communication with each other within the sheath 502 when one loop abuts an adjacent loop to form an electrical connection between loops in addition to the connection arising from the loops being formed from a common conductor. The sheath 502 may also be disposed over the conductor wire along the wound length of the conductor to electrically isolate one loop from an adjacent loop thereby maintaining a single electrical pathway along the conductor length from one loop to another without the formation of an electrical connection between abutting adjacent loops. The first sheath end 504 may also be proximate to the first conductor end 124 of FIG. 1, the second sheath end 506 may be proximate to the second conductor end 126 of FIG. 1, or both. For example, a first distance between the first sheath end 504 and the first conductor end 124 may satisfy (e.g., is less than or equal to) a threshold distance (e.g., 1 inch). A second distance between the second sheath end 506 and the second conductor end 126 may satisfy (e.g., is less than or equal to) the threshold distance (e.g., 1 inch). To illustrate, the sheath 502 may be disposed on or over the entire length of the conductor 122.

The first connector 110 of FIG. 1 may be coupled to the first conductor end 124 and to the first sheath end 504. For example, an outer surface of the first conductor end 124 may be covered by the first sheath end 504 and the covered first conductor end 124 may be coupled to the first connector 110. The second connector 112 of FIG. 1 may be coupled to the second conductor end 126 and to the second sheath end 506. For example, an outer surface of the second conductor end 126 may be covered by the second sheath end 506 and the covered second conductor end 126 may be coupled to the second connector 112.

In a particular embodiment, the first sheath end 504 may be proximate to the first conductor end 124 (or the second conductor end 126) and the second sheath end 506 may be distant from the second conductor end 126 (or the first conductor end 124). For example, a first distance between the first sheath end 504 and the first conductor end 124 (or the second conductor end 126) may satisfy (e.g., is less than or equal to) a threshold distance (e.g., 1 inch). A second distance between the second sheath end 506 and the second conductor end 126 (or the first conductor end 124) may fail to satisfy (e.g., is greater than) the threshold distance. To illustrate, the sheath 502 may be disposed on a portion of the conductor 122 that has greater proximity to the first conductor end 124 (or the second conductor end 126) than to the second conductor end 126 (or the first conductor end 124).

In a particular embodiment, the first sheath end 504 may be distant from the first conductor end 124 and the second sheath end 506 may be distant from the second conductor end 126. For example, each of the first distance and the second distance may fail to satisfy the threshold distance. To illustrate, the sheath 502 may be disposed on a middle portion of the conductor 122. In a particular embodiment, the LC tank 120 may be external to the sheath 502. For example, the sheath 502 may be disposed on a portion of the conductor 122 that excludes the LC tank 120.

The sheath 502 may be disposed over or on the LC tank 120. For example, the sheath 502 may be wrapped around a portion of the implantable lead assembly 102 that includes the LC tank 120. As another example, the sheath 502 may be pulled onto the implantable lead assembly 102 to cover a portion of the implantable lead assembly 102 that includes the LC tank 120. The LC tank 120 may be proximate to the first sheath end 504, the second sheath end 506, or both. For example, the LC tank 120 may extend from the first sheath end 504 to the second sheath end 506. To illustrate, the sheath 502 may be disposed on a portion of the conductor 122 that corresponds to the LC tank 120. The implantable lead assembly 102 may include one or more additional LC tanks that are not covered by the sheath 502, one or more additional LC tanks that are covered by the sheath 502, or a combination thereof. For example, the implantable lead assembly 102 may include a second conductor and the sheath 502 may also be disposed on a portion of the second conductor that corresponds to at least one additional LC tank.

The sheath 502 may form a protective barrier around at least a portion of the LC tank 120, at least a portion of the conductor 122, or both. For example, the sheath 502 may prevent bodily fluids of the patient 140 from contacting at least the portion of the LC tank 120, at least the portion of the conductor 122, or both.

Figure 6:
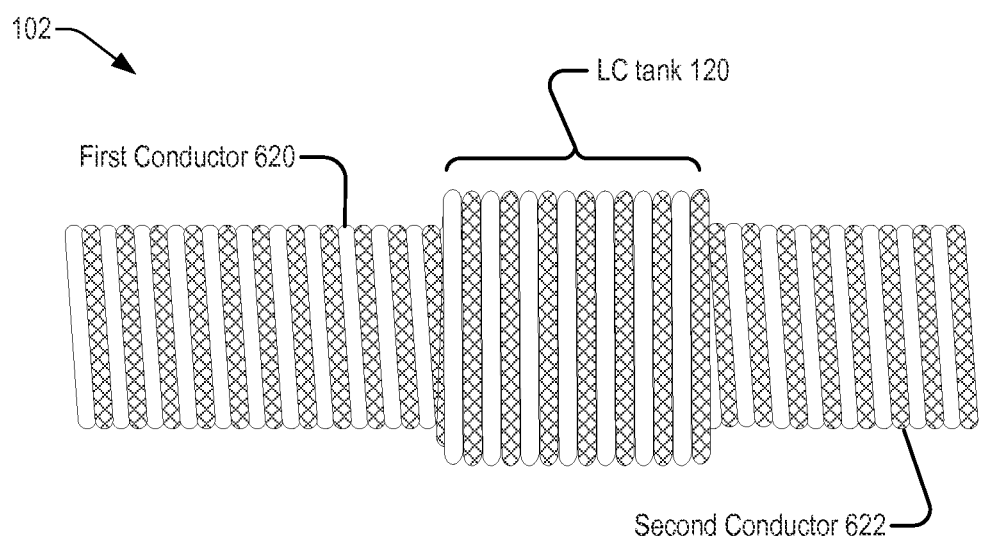
FIG. 6 is a diagram of another particular embodiment of the implantable lead assembly of FIG. 1 having an LC tank and a winding configuration.

Referring to FIG. 6, a diagram of another particular embodiment of the implantable lead assembly 102 is shown. The implantable lead assembly 102 may include the LC tank 120. The implantable lead assembly 102 may include at least one conductor. For example, the implantable lead assembly 102 may include a first conductor 620 and a second conductor 622. The first conductor 620, the second conductor 622, or both, may correspond to the conductor 122 of FIG. 1.

The first conductor 620, the second conductor 622, or both, may be coupled to the first connector 110 of FIG. 1. For example, the first conductor 620, the second conductor 622, or both, may be coupled, via the first connector 110, to the pulse generator 106 of FIG. 1. To illustrate, a first conductor end of the first conductor 620 may be coupled via the first connector 110 to the pulse generator 106, a first conductor end of the second conductor 622 may be coupled via the first connector 110 to the pulse generator 106, or both. The first conductor 620, the second conductor 622, or both, may be coupled to the second connector 112 of FIG. 1. For example, the first conductor 620, the second conductor 622, or both, may be coupled, via the second connector 112, to the electrode 104 of FIG. 1. To illustrate, a second conductor end of the first conductor 620 may be coupled via the second connector 112 to the electrode 104, a second conductor end of the second conductor 622 may be coupled via the second connector 112 to the electrode 104, or both.

The implantable lead assembly 102 may include one or more LC tanks. For example, the implantable lead assembly 102 may include the LC tank 120. The LC tank 120 may be coupled to the first conductor 620 and to the second conductor 622. For example, the LC tank 120 may include a first LC tank formed by winding the first conductor 620 (e.g., as described with reference to FIGS. 10-12) and may include a second LC tank formed by winding the second conductor 622 (e.g., as described with reference to FIGS. 10-12). The first LC tank and the second LC tank may be nested (or interleaved) next to each other to reduce an outer diameter of the implantable lead assembly 102. In a particular embodiment, the first LC tank and the second LC tank may be coupled to distinct electrodes. For example, the first conductor 620 and the first LC tank may be coupled, via the second connector 112, to the electrode 104, and the second conductor 622 and the second LC tank may be coupled, via another connector, to another electrode.

An impedance of the implantable lead assembly 102 may be based on a capacitance of the implantable lead assembly 102, an inductance of the implantable lead assembly 102, a frequency of the external electro-magnetic field 132 of FIG. 1, or a combination thereof. The capacitance of the implantable lead assembly 102 may be based on a capacitance of one or more LC tanks of the implantable lead assembly 102, a capacitance of one or more conductors of the implantable lead assembly 102, or a combination thereof. For example, the capacitance of the implantable lead assembly 102 may be based on a capacitance of the LC tank 120, a capacitance of the first conductor 620, a capacitance of the second conductor 622, or a combination thereof.

The inductance of the implantable lead assembly 102 may be based on an inductance of one or more LC tanks of the implantable lead assembly 102, an inductance of one or more conductors of the implantable lead assembly 102, or a combination thereof. For example, the inductance of the implantable lead assembly 102 may be based on an inductance of the LC tank 120, an inductance of the first LC tank, an inductance of the second conductor 622, or a combination thereof.

An impedance of the implantable lead assembly 102 including the LC tank 120 (or the first LC tank and the second LC tank) may satisfy an impedance threshold when the external electro-magnetic field 132 has a first frequency and when the external electro-magnetic field 132 has a second frequency. For example, the implantable lead assembly 102 including the LC tank 120 (e.g., formed as described with reference to FIGS. 10-12) may have impedance characteristics as described with reference to FIG. 4. The implantable lead assembly 102 may be thus enable safe MRI procedures at the first frequency or at the second frequency.

Figure 7:
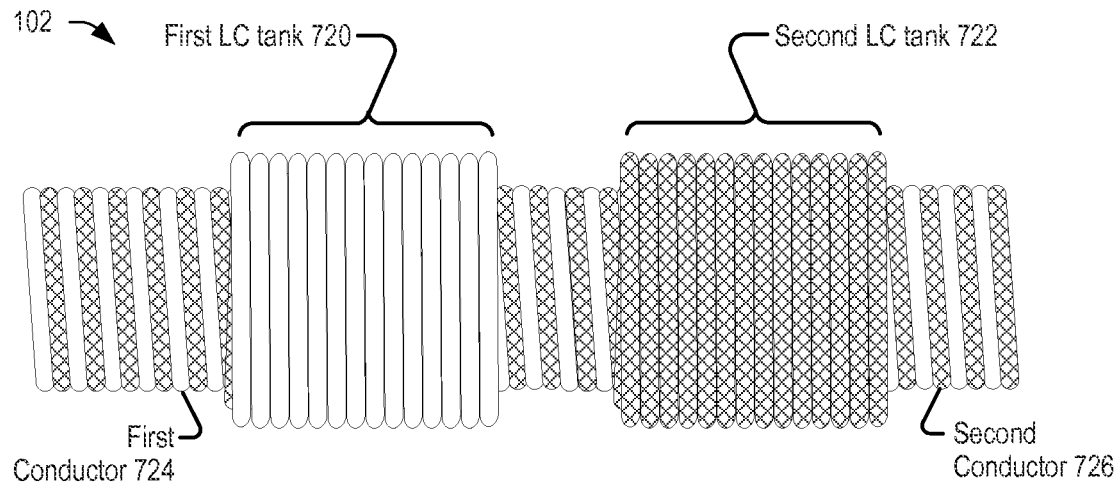
FIG. 7 is a diagram of another particular embodiment of the implantable lead assembly of FIG. 1 having multiple LC tanks and a winding configuration.

Referring to FIG. 7, a diagram of another particular embodiment of the implantable lead assembly 102 is shown. The implantable lead assembly 102 may include multiple LC tanks. For example, the implantable lead assembly 102 may include a first LC tank 720 and a second LC tank 722. In a particular embodiment, the implantable lead assembly 102 may include more than two LC tanks. The first LC tank 720 or the second LC tank 722 may correspond to the LC tank 120 of FIG. 1.

One or more of the multiple LC tanks may be disposed at distinct locations along an axis to improve (e.g., increase) heat dissipation. For example, the first LC tank 720 and the second LC tank 722 may be disposed at distinct locations along an axis (e.g., horizontal axis (or x-axis) of the implantable lead assembly 102. The first LC tank 720 may be coupled to a first conductor 724. For example, the first LC tank 720 may be formed by winding the first conductor 724 (e.g., as described with reference to FIGS. 10-12). The second LC tank 722 may be coupled to a second conductor 726. For example, the second LC tank 722 may be formed by winding the second conductor 726 (e.g., as described with reference to FIGS. 10-12). In a particular embodiment, the implantable lead assembly 102 may include more than two conductors (e.g., the first conductor 724 and the second conductor 726).

The first conductor 724, the second conductor 726, or both, may be coupled to the first connector 110 of FIG. 1. For example, the first conductor 724, the second conductor 726, or both, may be coupled, via the first connector 110, to the pulse generator 106 of FIG. 1. To illustrate, a first conductor end of the first conductor 724 may be coupled via the first connector 110 to the pulse generator 106, a first conductor end of the second conductor 726 may be coupled via the first connector 110 to the pulse generator 106, or both. The first conductor 724, the second conductor 726, or both, may be coupled to the second connector 112 of FIG. 1. For example, the first conductor 724, the second conductor 726, or both, may be coupled, via the second connector 112, to the electrode 104 of FIG. 1. To illustrate, a second conductor end of the first conductor 724 may be coupled via the second connector 112 to the electrode 104, a second conductor end of the second conductor 726 may be coupled via the second connector 112 to the electrode 104, or both.

In a particular embodiment, the first LC tank 720 and the second LC tank 722 may be coupled to distinct electrodes. For example, the second conductor end of the first conductor 724 may be coupled via the second connector 112 to the electrode 104, and the second conductor end of the second conductor 726 may be coupled via another connector to another electrode.

An impedance of the implantable lead assembly 102 including the first LC tank 720 and the second LC tank 722 may satisfy an impedance threshold when the external electro-magnetic field 132 has a first frequency and when the external electro-magnetic field 132 has a second frequency. For example, the implantable lead assembly 102 including the first LC tank 720 (e.g., formed as described with reference to FIGS. 10-12) and the second LC tank 722 (e.g., formed as described with reference to FIGS. 10-12) may have impedance characteristics described with reference to FIG. 4. The implantable lead assembly 102 may be thus enable safe MRI procedures at the first frequency or at the second frequency.

Figure 8:
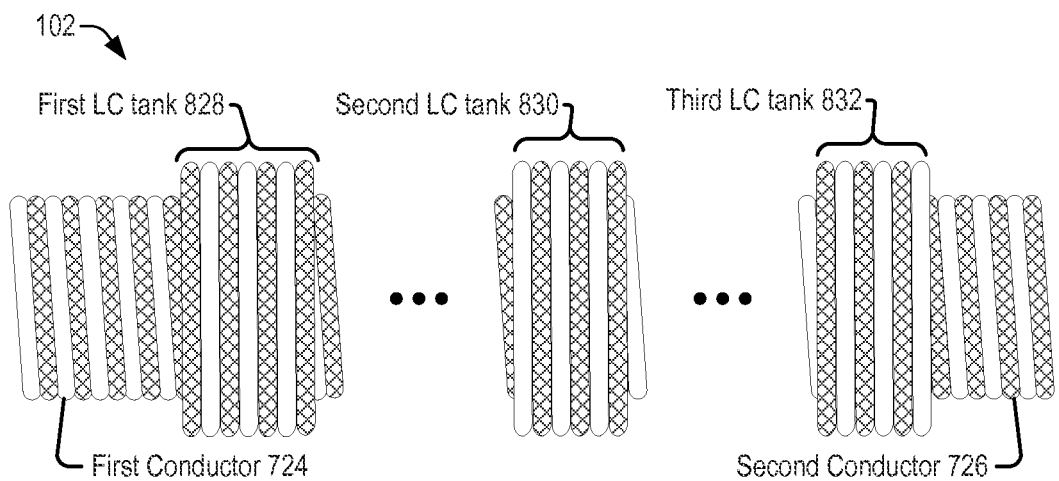
FIG. 8 is a diagram of another particular embodiment of the implantable lead assembly of FIG. 1 having multiple LC tanks and a winding configuration.

Referring to FIG. 8, a diagram of another particular embodiment of the implantable lead assembly 102 is shown. The implantable lead assembly 102 may include multiple LC tanks. For example, the implantable lead assembly 102 may include a first LC tank 828, a second LC tank 830, and a third LC tank 832. In a particular embodiment, the implantable lead assembly 102 may include fewer than three LC tanks or more than three LC tanks. The first LC tank 828, the second LC tank 830, or the third LC tank 832 may correspond to the LC tank 120 of FIG. 1.

An LC tank may be coupled to a plurality of conductors. For example, the first LC tank 828, the second LC tank 830, and the third LC tank 832 may be coupled to the first conductor 724 and to the second conductor 726. For example, the first LC tank 828 may be formed by winding a first portion of the first conductor 724 and a first portion of the second conductor 726 (e.g., as described with reference to FIGS. 10-12). The second LC tank 830 may be formed by winding a second portion of the first conductor 724 and a second portion of the second conductor 726. The third LC tank 832 may be formed by winding a third portion of the first conductor 724 and a third portion of the second conductor 726. The first LC tank 828, the second LC tank 830, and the third LC tank 832 may be disposed at different locations along an axis (e.g., horizontal axis (or x-axis) of the implantable lead assembly 102 to improve (e.g., increase) heat dissipation. For example, the first portion, the second portion, and the third portion of the first conductor 724 (or the second conductor 726) may correspond to distinct locations of the implantable lead assembly 102. In a particular embodiment, an LC tank may be coupled to fewer than or more than two conductors (e.g., the first conductor 724 and the second conductor 726).

An LC tank may include multiple nested LC tanks. For example, the first LC tank 828 may include a first LC tank nested (or interleaved) with a second LC tank. The first LC tank may be formed by winding a first portion of the first conductor 724 (e.g., as described with reference to FIGS. 10-12). The second LC tank may be formed by winding a second portion of the second conductor 726 (e.g., as described with reference to FIGS. 10-12). The first portion and the second portion may be interleaved during winding. The first portion and the second portion may correspond to the same location along the implantable lead assembly 102.

An impedance of the implantable lead assembly 102 including the first LC tank 828, the second LC tank 830, and the third LC tank 832 may satisfy an impedance threshold when the external electro-magnetic field 132 has a first frequency and when the external electro-magnetic field 132 has a second frequency. For example, the implantable lead assembly 102 including the first LC tank 828 (e.g., formed as described with reference to FIGS. 10-12), the second LC tank 830 (e.g., formed as described with reference to FIGS. 10-12), and the third LC tank 832 (e.g., formed as described with reference to FIGS. 10-12) may have impedance characteristics described with reference to FIG. 4. The implantable lead assembly 102 may be thus enable safe MRI procedures at the first frequency or at the second frequency.

Figure 9:
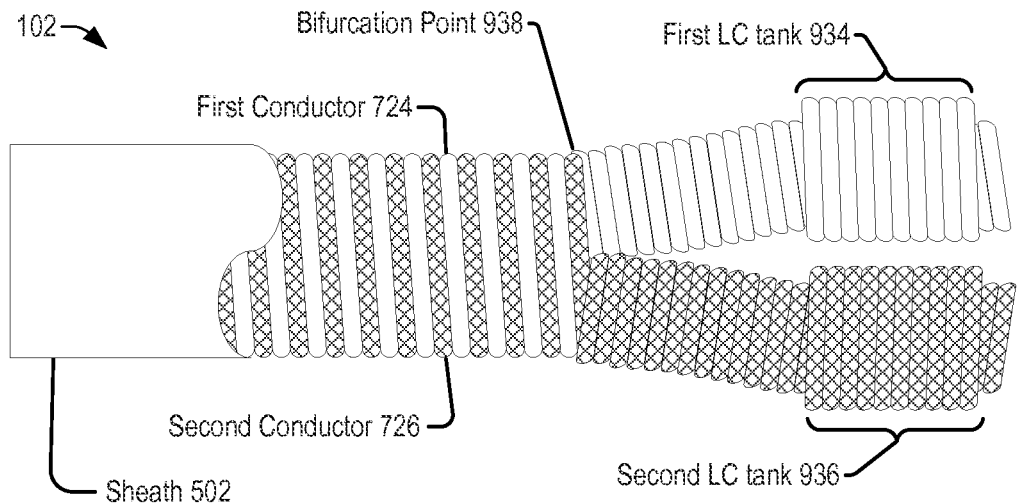
FIG. 9 is a diagram of another particular embodiment of the implantable lead assembly of FIG. 1 having multiple LC tanks and a winding configuration.

Referring to FIG. 9, a diagram of another particular embodiment of the implantable lead assembly 102 is shown. The implantable lead assembly 102 may include multiple LC tanks (e.g., a first LC tank 934 and a second LC tank 936). The first LC tank 934 or the second LC tank 936 may correspond to the LC tank 120 of FIG. 1. The first LC tank 934 may be coupled to the first conductor 724. For example, the first LC tank 934 may be formed by winding a portion of the first conductor 724 (e.g., as described with reference to FIGS. 10-12). The second LC tank 936 may be coupled to the second conductor 726. For example, the second LC tank 936 may be formed by winding a portion of the second conductor 726 (e.g., as described with reference to FIGS. 10-12). The implantable lead assembly 102 may include the sheath 502. The sheath 502 may be disposed over or on at least a portion of the first conductor 724, at least a portion of the second conductor 726, at least a portion of the first LC tank 934, at least a portion of the second LC tank 936, or a combination thereof.

The implantable lead assembly 102 may include a bifurcation point 938. The first conductor 724 may be interleaved with the second conductor 726 prior to the bifurcation point 938. The first conductor 724 and the second conductor 726 may be bifurcated subsequent to the bifurcation point 938. For example, the first conductor 724 and the second conductor 726 may not be interleaved subsequent to the bifurcation point 938. In a particular embodiment, the sheath 502 may be disposed on or over the implantable lead assembly 102 prior to the bifurcation point 938.

An impedance of the implantable lead assembly 102 including the first LC tank 934 and the second LC tank 936 may satisfy an impedance threshold when the external electro-magnetic field 132 has a first frequency and when the external electro-magnetic field 132 has a second frequency. For example, the implantable lead assembly 102 including the first LC tank 828 (e.g., formed as described with reference to FIGS. 10-12) and the second LC tank 830 (e.g., formed as described with reference to FIGS. 10-12) may have impedance characteristics described with reference to FIG. 4. The implantable lead assembly 102 may be thus enable safe MRI procedures at the first frequency or at the second frequency.

Figure 10:
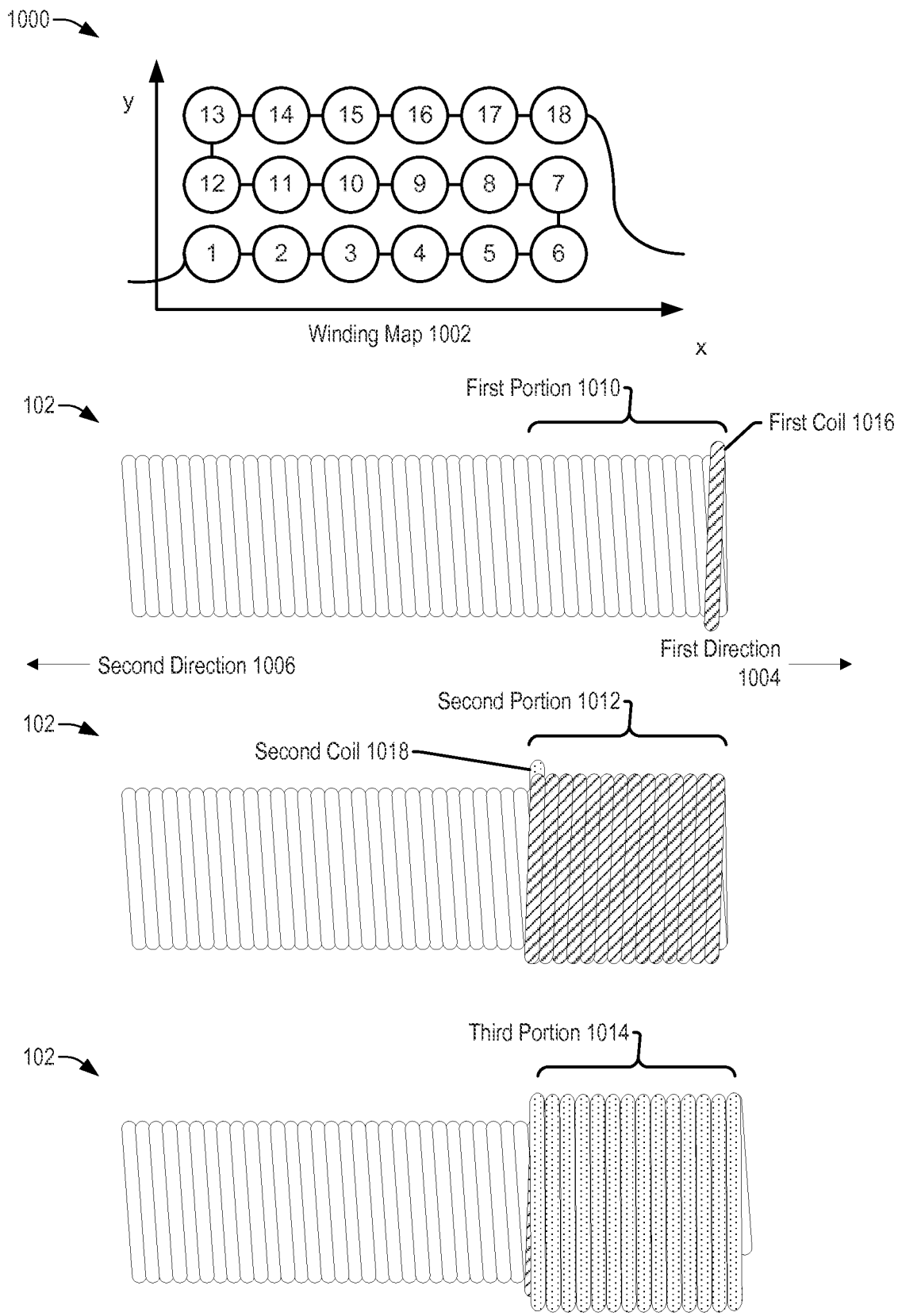
FIG. 10 is a diagram illustrating a winding technique to form an LC tank of the implantable lead assembly of FIG. 1.
Figure 11:
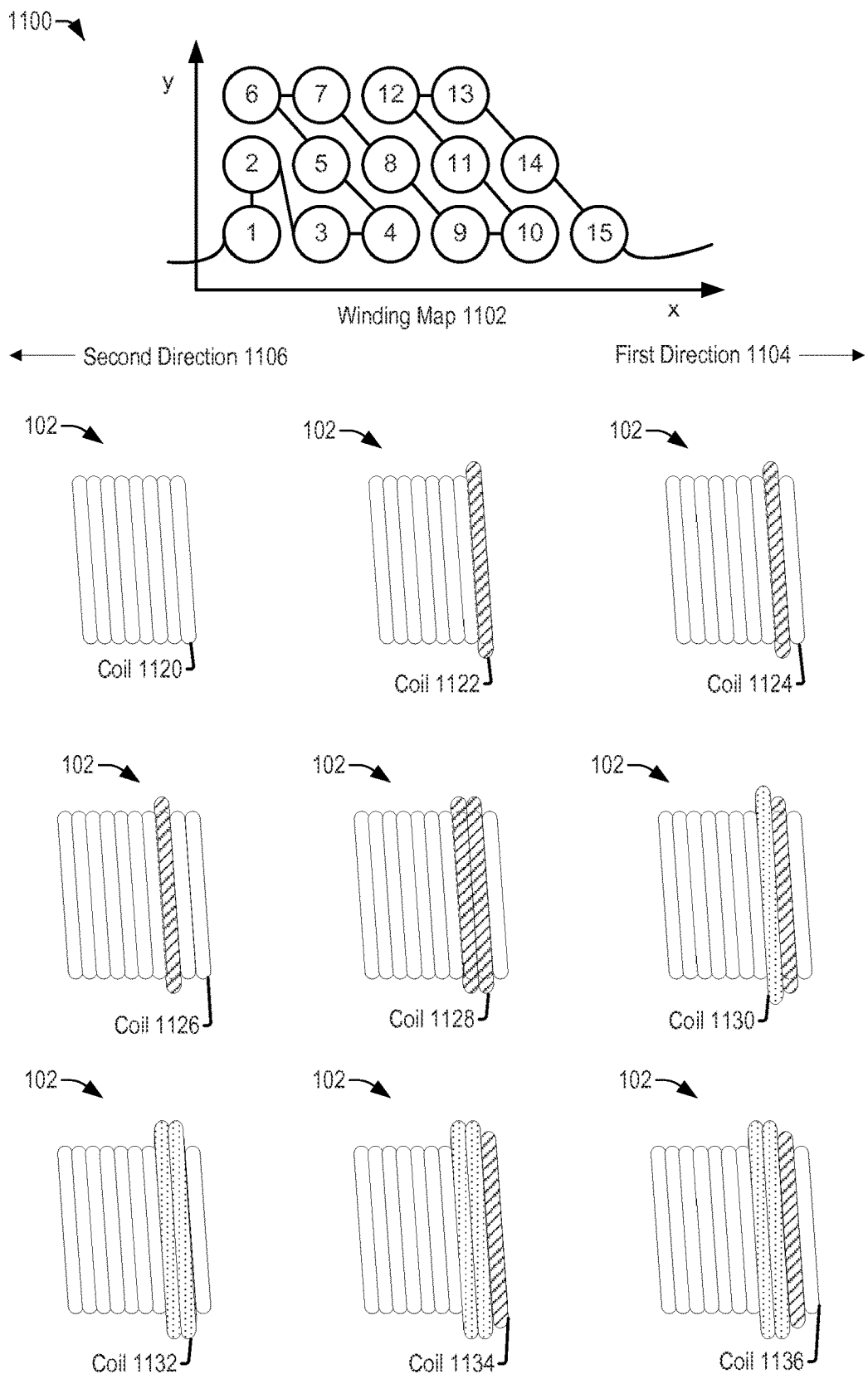
FIG. 11 is a diagram illustrating another winding technique to form an LC tank of the implantable lead assembly of FIG. 1.
Figure 12:
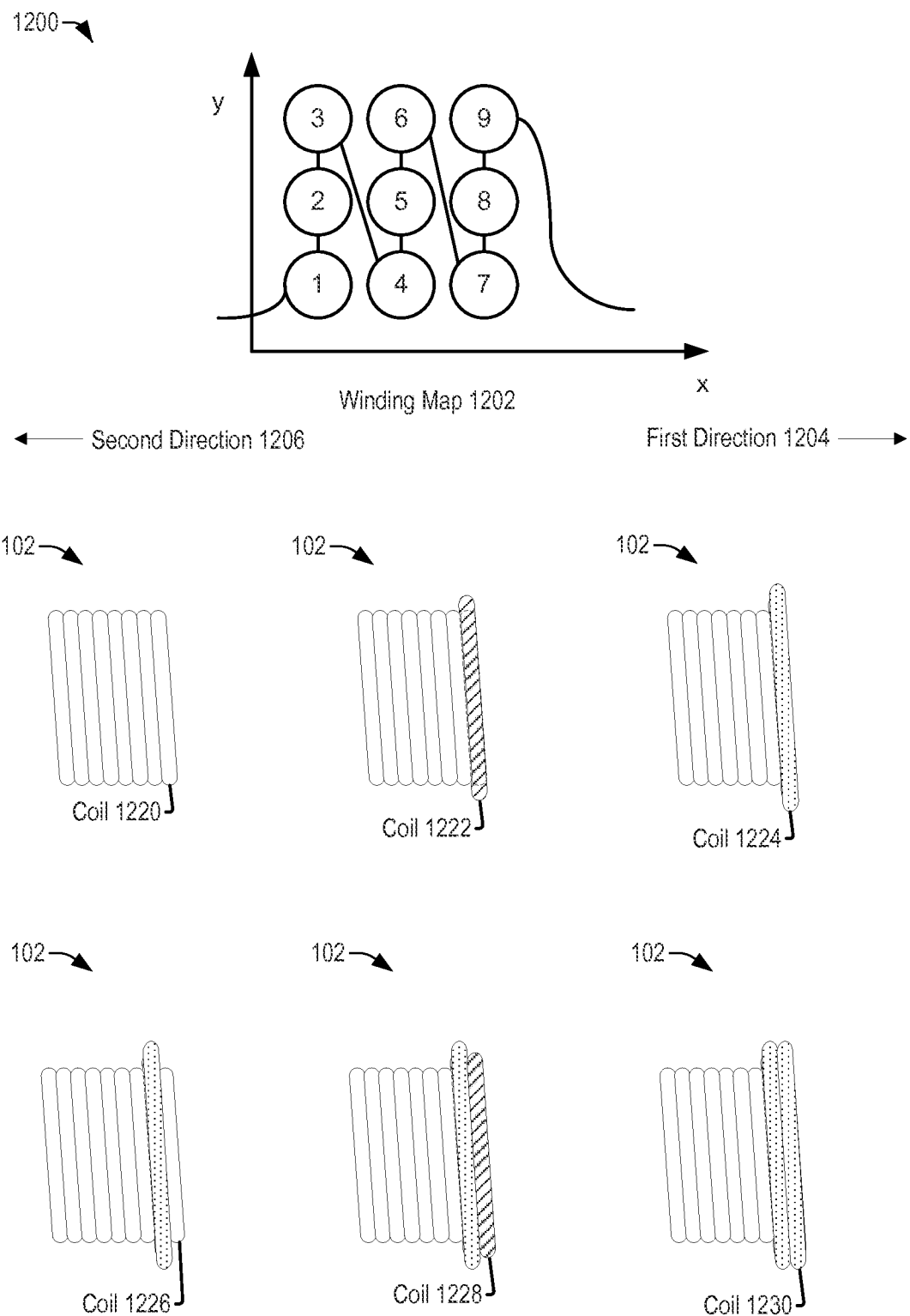
FIG. 12 is a diagram illustrating another winding technique to form an LC tank of the implantable lead assembly of FIG. 1.

FIGS. 10-12 illustrate examples of winding techniques and LC tanks (e.g., the LC tank 120) formed using the winding techniques. FIGS. 10-12 are for illustration. It should be understood that in some embodiments other winding techniques may be used to form an LC tank (e.g., the LC tank 120 of FIG. 1, the first LC tank 720, the second LC tank 722 of FIG. 7, the first LC tank 828, the second LC tank 830, the third LC tank 832 of FIG. 8, the first LC tank 934, or the second LC tank 936 of FIG. 9), such as winding techniques used in fabric arts, rope making, weaving, etc. In particular, the winding technique illustrated in FIG. 8 can be modified to have a single conductor (first conductor 724) wound with another material that is not conductive (electrically insulating) or significantly less conductive than first conductor 724. In such a configuration illustrated in FIG. 8, the second conductor 726 may be considered to be non-conductive or an insulator to provide electrical isolation between each loop formed by the first conductor 724, thereby allowing an uninsulated first conductor 724 to be wound with an interposed insulator (designated as second conductor 726 in FIG. 8) with or without the use of an insulating coating disposed over the first conductor 724. As can be appreciated, when the first conductor 724 wraps over itself to form an LC tank (such as LC tanks 828, 830, and 832) an insulating sleeve may be interested between the overwrapping layers to maintain electrical isolation between adjacent or abutting loops of first conductor 724.

Referring to FIG. 10, a diagram illustrating a winding technique is shown and generally designated 1000. The diagram 1000 includes a winding map 1002 corresponding to the winding technique, with the winding map 1002 illustrating a cross-section view of the wound conductor 724, 726 with "x" designating an axial direction of the lead assembly 102 and "y" designating a radial direction extending away from an axis defined by the lead assembly 102 (not shown). The winding technique may be used to form at least one LC tank of the implantable lead assembly 102. The winding map 1002 illustrates a path of a conductor (e.g., the conductor 122). For example, the conductor 122 may be wound to follow the path from point 1 to point 18 of the winding map 1002, with points 1-6 representing an inner layer, points 7-12 representing a middle layer overwrapping points 1-6, and points 13-18 representing an outer layer overwrapping points 7-12 to form the wound conductor configuring providing the LC tank.

A first portion 1010 of the conductor 122 may be wound (e.g., coiled) in a first direction 1004. For example, coils of the first portion 1010 may correspond to point 1-point 6 of the winding map 1002. The coils of the first portion 1010 may have a first diameter. The coils of the first portion 1010 may define a cavity. A core insert may be disposed in the cavity, as described with reference to FIG. 1.

A second portion 1012 may be wound (e.g., coiled) in a second direction 1006. The second direction 1006 may be reverse of the first direction 1004. The second portion 1012 may overlap the first portion 1010. Coils of the second portion 1012 may correspond to point 7-point 12 of the winding map 1002. For example, a first coil 1016 may correspond to point 7 of the winding map 1002. The coils of the second portion 1012 may have a second diameter. The second diameter may be larger than the first diameter.

A third portion 1014 may be coiled in the first direction 1004. The third portion 1014 may overlap the second portion 1012. Coils of the third portion 1014 may correspond to point 13-point 18 of the winding map 1002. For example, a second coil 1018 may correspond to point 13 of the winding map 1002. The coils of the third portion 1014 may have a third diameter. The third diameter may be larger than the second diameter. In a particular embodiment, the first portion 1010, the second portion 1012, the third portion 1014, or a combination thereof, may include fewer coils or more coils than illustrated in FIG. 10. The LC tank 120 may include the first portion 1010, the second portion 1012, and the third portion 1014. In a particular embodiment, the LC tank 120 may include more than three portions.

Referring to FIG. 11, a diagram illustrating a winding technique is shown and generally designated 1100. The diagram 1100 includes a winding map 1102 corresponding to the winding technique. The winding technique may be used to form at least one LC tank of the implantable lead assembly 102. The winding map 1102 illustrates a path of a conductor (e.g., the conductor 122). For example, the LC tank 120 may be formed by winding the conductor 122 to follow the path from point 1 to point 15 of the winding map 1102.

The conductor 122 may be wound (e.g., coiled) in a first direction 1104 (e.g., forward). The conductor 122 may be coiled in the first direction 1104 to form a coil 1120 and may be coiled around the coil 1120 to form a coil 1122. The coil 1120 may correspond to point 1 of the winding map 1102. The coil 1122 may correspond to point 2 of the winding map 1102. The coil 1122 may have a larger diameter than the coil 1120. The conductor 122 may be wound in the first direction 1104 and may be coiled to form a coil 1124. The coil 1124 may correspond to point 3 of the winding map 1102. The conductor 122 may be wound in the first direction 1104 and coiled to form a coil 1126. The coil 1126 may correspond to point 4 of the winding map 1102.

The conductor 122 may be wound in a second direction 1106 (e.g., backward) and may be coiled around the coil 1124 to form a coil 1128. The coil 1128 may correspond to point 5 of the winding map 1102. The coil 1128 may have a larger diameter than the coil 1124. The second direction 1106 may be reverse of the first direction 1104.

The conductor 122 may be wound in the second direction 1106 and may be coiled around the coil 1122 to form a coil 1130. The coil 1130 may correspond to point 6 of the winding map 1102. The coil 1130 may have a larger diameter than the coil 1122.

The conductor 122 may be wound in the first direction 1104 and may be coiled around the coil 1128 to form a coil 1132. The coil 1132 may correspond to point 7 of the winding map 1102. The coil 1132 may have a larger diameter than the coil 1128. The conductor 122 may be wound in the first direction 1104 and may be coiled around the coil 1126 to form a coil 1134. The coil 1134 may correspond to point 8 of the winding map 1102. The coil 1134 may have a larger diameter than the coil 1126. The conductor 122 may be wound in the first direction 1104 and may be coiled to form a coil 1136. The coil 1136 may correspond to point 9 of the winding map 1102.

One or more coils of the LC tank 120 may define a cavity. For example, the coil 1120, the coil 1126, and the coil 1132 may define a cavity. A core insert may be disposed in the cavity, as described with reference to FIG. 1. For example, the core insert may be disposed in one or more of the coil 1120, the coil 1126, and the coil 1132.

Referring to FIG. 12, a diagram illustrating a winding technique is shown and generally designated 1200. The diagram 1200 includes a winding map 1202 corresponding to the winding technique. The winding technique may be used to form at least one LC tank of the implantable lead assembly 102. The winding map 1202 illustrates a path of a conductor (e.g., the conductor 122). For example, the LC tank 120 may be formed by winding the conductor 122 to follow the path from point 1 to point 9 of the winding map 1202.

The conductor 122 may be wound (e.g., coiled) in a first direction 1204 (e.g., forward) to form a coil 1220. The coil 1220 may correspond to point 1 of the winding map 1202. The conductor 122 may be coiled around the coil 1220 to form a coil 1222 and may be coiled around the coil 1222 to form a coil 1224. The coil 1222 and the coil 1224 may correspond to point 2 and point 3 of the winding map 1202 respectively.

The conductor 122 may be wound in the first direction 1204 and may be coiled to form a coil 1226. The coil 1226 may correspond to point 4 of the winding map 1202. The conductor 122 may be coiled around the coil 1226 to form a coil 1228 and may be coiled around the coil 1228 to form a coil 1230. The coil 1228 and the coil 1230 may correspond to point 5 and point 6 of the winding map 1202 respectively.

One or more of the coils of the conductor 122 may define a cavity. For example, the coil 1220 and the coil 1226 may define a cavity. A core insert may be disposed in the cavity, as described with reference to FIG. 1.

The LC tank (e.g., the LC tank 120) formed using the winding techniques described with reference to FIGS. 10-12 may configure the implantable lead assembly 102 to have an impedance that satisfies an impedance threshold when an external electro-magnetic field 132 has a first frequency (e.g., approximately 64 MHz) and satisfies the impedance threshold when the external electro-magnetic field 132 has a second frequency (e.g., approximately 128 MHz). The implantable lead assembly 102 including the LC tank 120 may be considered compatible with an MRI system corresponding to the first frequency, the second frequency, or both. For example, the implantable lead assembly 102 may be considered compatible with a 1.5 T MRI system, 3 T MRI system, or both.

Figure 13:
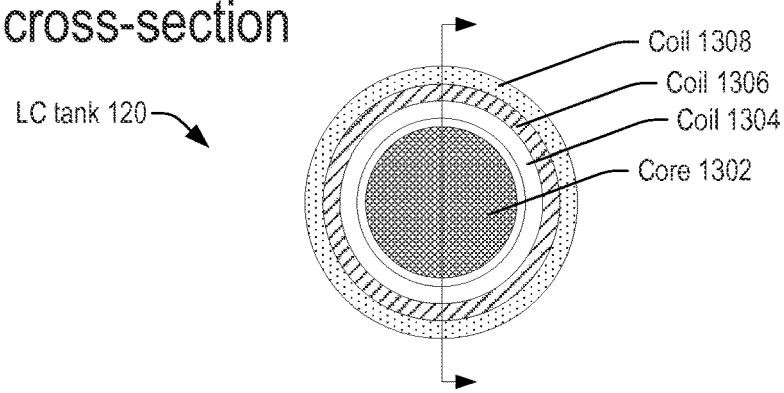
FIG. 13 is a diagram of cross-sections of the implantable lead assembly of FIG. 1 having an LC tank and a winding configuration.
Figure 13:
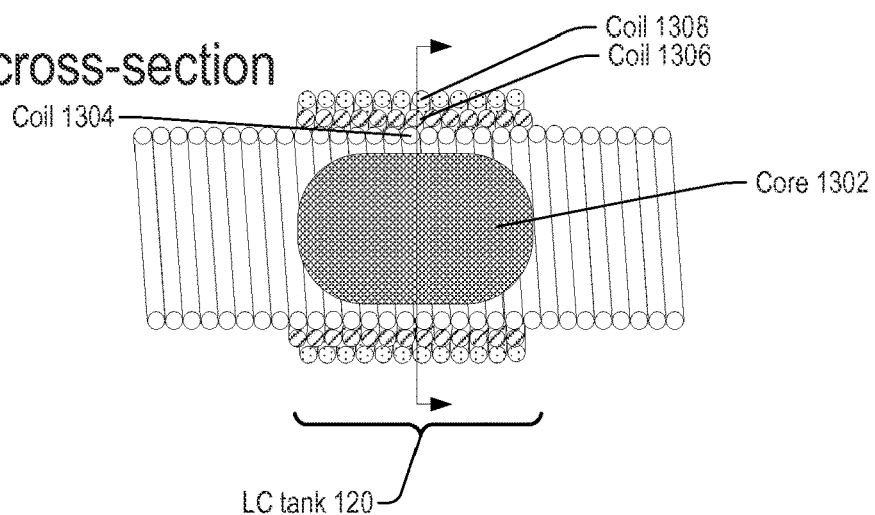

Referring to FIG. 13, a diagram of cross-sections of the implantable lead assembly 102 is shown and generally designated 1300. The diagram 1300 includes an end cross-section and a side cross section of the LC tank 120. The LC tank 120 includes a core 1302. The core 1302 may include an air core, a metallic core, or a non-metallic core. For example, a core insert may be disposed in a cavity formed by a coil 1304. The core insert may be non-metallic. The core insert may include at least one of iron, silver, platinum, gold, tungsten, or iridium. The core insert may include a metal alloy including at least one of iron, silver, platinum, gold, tungsten, or iridium. The core insert may include iron-platinum (Fe—Pt) pellets.

The coil 1304 may overlap the core 1302. A coil 1306 may overlap the coil 1304. A coil 1308 may overlap the coil 1306. The coils 1304, 1306, and 1308 may be formed by winding the conductor 122 of FIG. 1, e.g., as described with reference to FIGS. 10-12.

Figure 14:
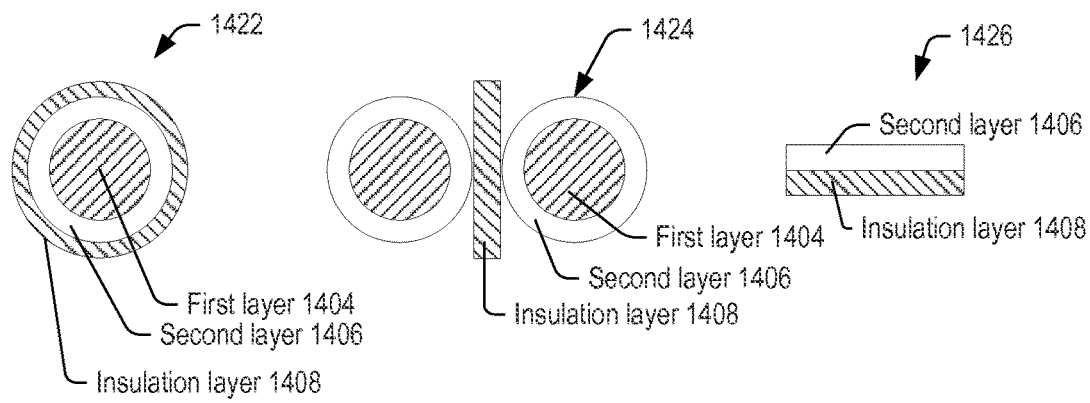
FIG. 14 is a diagram of particular embodiments of a conductor of the system of FIG. 1 having an LC tank and a winding configuration.

Referring to FIG. 14, a diagram of particular embodiments of a conductor is shown and generally designated 1400. The diagram 1400 illustrates cross-sections of a conductor 1422, a conductor 1424, and a conductor 1426. The conductor 1422, the conductor 1424, or the conductor 1426 may correspond to one or more conductors of the implantable lead assembly 102 of FIG. 1. For example, the conductor 1422, the conductor 1424, or the conductor 1426 may correspond to the conductor 122 of FIG. 1.

The conductor 1422 may include a first layer 1404, a second layer 1406, and an insulation layer 1408. The first layer 1404 may include a conductor. The first layer 1404 may include a metal or a metal alloy. For example, the first layer 1404 may include at least one of silver (Ag), copper (Cu), gold (Au), or aluminum (Al). A particular metal may be selected to form the first layer 1404 based on thermal conductivity of the particular metal, cost of the particular metal, or both. For example, silver may have higher thermal conductivity than copper. Copper may be more cost-effective than silver. The second layer 1406 may be disposed on or over the first layer 1404. The second layer 1406 may include a nickel cobalt alloy. The nickel cobalt alloy may be corrosion-resistant. The insulation layer 1408 may be an insulation coating disposed on or over the second layer 1406. An LC tank (e.g., the LC tank 120 of FIG. 1) formed by winding the conductor 1422 may include two insulating layers between adjacent windings (or coils). For example, the insulation layer 1408 of a first coil and the insulation layer 1408 of a second coil may be between the first coil and the second coil when the first coil is adjacent to the second coil.

The conductor 1424 may include the second layer 1406 disposed on or over the first layer 1404. The insulation layer 1408 may be disposed between adjacent coils of the conductor 1422. An LC tank (e.g., the LC tank 120 of FIG. 1) formed by winding the conductor 1424 may include a single insulating layer (e.g., the insulation layer 1408) between adjacent windings (or coils).

The conductor 1426 includes the second layer 1406 on one side and the insulation layer 1408 on the opposite side. The conductor 1426 may be wound to form the LC tank 120 such that the insulation layer 1408 of one winding overlaps the second layer 1406 of an adjacent winding. An LC tank (e.g., the LC tank 120 of FIG. 1) formed by winding the conductor 1424 may include a single insulating layer (e.g., the insulation layer 1408) between adjacent windings (or coils). The conductor 1426 may have a shape (e.g., a flat tape-like shape) such that the conductor 1426 assumes an orientation during winding. The insulation layer 1408 may be placed on the conductor 1426 based on the orientation so that when the conductor 1426 is wound (e.g., as described with reference to FIGS. 10-12) to form the LC tank 120, the insulation layer 1408 separates adjacent coils or windings of the conductor 1426.

The insulation layer 1408 may be added during winding of a conductor (e.g., the conductor 1422, the conductor 1424, or the conductor 1426) to form the LC tank 120. The insulation layer 1408 may be a separate structure from the conductor (e.g., the conductor 1422, the conductor 1424, or the conductor 1426). For example, the insulation layer 1408 may be disposed on a first coil (or a first winding) of the LC tank 120 prior to overlapping the first coil (or the first winding) with a second coil (or a second winding). The insulation layer 1408 may be a viscous liquid that is added during winding of the conductor (e.g., the conductor 1422, the conductor 1424, or the conductor 1426).

The insulation layer 1408 may prevent current from skipping from coil to coil of the LC tank 120. The conductor (e.g., the conductor 1422, the conductor 1424, or the conductor 1426) may have a parasitic capacitance between a first coil and a second coil separated by the insulation layer 1408.

Although the description above contains many specificities, these specificities are utilized to illustrate some of the exemplary embodiments of this disclosure and should not be construed as limiting the scope of the disclosure. The scope of this disclosure should be determined by the claims, their legal equivalents. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. § 112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system.

As noted above, embodiments within the scope of the present disclosure include program products comprising computer readable storage device, or machine-readable media for carrying, or having machine-executable instructions or data structures stored thereon. Such machine-readable media can be any available media which can be accessed by a general purpose or special purpose computer or other machine with a processor. By way of example, such machine-readable media can comprise RAM, ROM, EPROM, EEPROM, CD ROM or other optical disk storage, magnetic disk storage or other magnetic storage devices, or any other medium which can be used to carry or store program code in the form of machine-executable instructions or data structures and which can be accessed by a general purpose or special purpose computer or other machine with a processor. The disclosure may be utilized in a non-transitory media. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing descriptions of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. An implantable lead comprising:
a conductor having a conductor length extending from a first end to a second end of the conductor;
a sheath having a sheath length extending from a first end to a second end of the sheath, the sheath disposed over the conductor from the conductor first end to the conductor second end; and
opposing first and second lead ends, the first lead end coupled to the first ends of the conductor and sheath and the second lead end coupled to the second ends of the conductor and sheath,
wherein the conductor has a first portion at the first end of the conductor and a second portion at the second end of the conductor and an inductor-capacitor portion disposed between the first and second portions, the first and second portions having a single length of the conductor disposed within the sheath, the inductor-capacitor portion having at least three lengths of the conductor disposed proximate to each other to define an LC tank, the LC tank being tuned to resonate at a frequency of approximately 90-102 MHz when exposed to a first external magnetic field having a first frequency of 64 MHz and a second external magnetic field having a second frequency of 128 MHz, the LC tank being further tuned to provide approximately 1 kOhm of impedance when exposed to the first external magnetic field and the second external magnetic field.

2. The implantable lead of claim 1, wherein at least one of the at least three lengths is configured as a coiled winding that defines a core of the inductor-capacitor portion.

3. The implantable lead of claim 2, wherein another one of the at least three lengths is disposed at the core.

4. The implantable lead of claim 2, wherein the inductor-capacitor portion is configured to define a cavity at the core.

5. The implantable lead of claim 2, the implantable lead further comprising a non-metallic core insert disposed at the core.

6. The implantable lead of claim 2, the implantable lead further comprising a metallic core insert disposed at the core, the core insert including Fe-PT pellets.

7. The implantable lead of claim 2, the implantable lead further comprising a metallic core insert disposed at the core, the metallic core including at least one of iron, platinum, gold, tungsten, and iridium.

8. The implantable lead of claim 1, wherein the conductor includes an inner layer encased by an outer layer, the inner layer comprising silver and the outer layer comprising a nickel cobalt alloy.

9. An implantable lead comprising:
a conductor having a conductor length extending from a first end to a second end of the conductor, the conductor further having a straight portion coupled to an inductor-capacitor portion, the straight portion having a straight length of the conductor, the inductor-capacitor portion having a coiled length of the conductor defining an internal core of the inductor-capacitor portion; and
a core insert disposed at the internal core,
wherein the inductor-capacitor portion and the core insert together define an LC tank, the LC tank being tuned to resonate at a frequency of approximately 90-102 MHz when exposed to a first external magnetic field having a frequency of 64 MHz and a second external magnetic field having a frequency of 128 MHz, the LC tank being further tuned to provide approximately 1 kOhm of impedance when exposed to the first external magnetic field and the second external magnetic field.

10. The implantable lead of claim 9, wherein the coiled length is overwrapped by an additional length of the conductor.

11. The implantable lead of claim 10, wherein at least a portion of the additional length is coiled.

12. The implantable lead of claim 11, wherein the coiled length is intertwined with an additional length of the conductor.

13. The implantable lead of claim 12, wherein at least a portion of the additional length is coiled.

14. The implantable lead of claim 9, wherein the core insert is metallic.

15. The implantable lead of claim 14, wherein the metallic core includes at least one of iron, platinum, gold, tungsten, and iridium.

16. The implantable lead of claim 15, wherein the core insert includes Fe-PT pellets.

17. The implantable lead of claim 9, wherein the conductor includes an inner layer encased by an outer layer, the inner layer comprising silver and the outer layer comprising a nickel cobalt alloy.

18. An implantable medical device comprising:
a pulse generator having a port; and
a lead coupled to the port, the lead comprising:
a conductor having a conductor length extending from a first end to a second end of the conductor, the conductor further having a straight portion coupled to an inductor-capacitor portion, the straight portion having a straight length of the conductor, the inductor-capacitor portion having a coiled length of the conductor defining an internal core of the inductor-capacitor portion, and
a core insert disposed at the internal core,
wherein the inductor-capacitor portion and the core insert together define an LC tank, the LC tank being tuned to resonate at a frequency of approximately 90-102 MHz when exposed to a first external magnetic field having a frequency of 64 MHz and a second external magnetic field having a frequency of 128 MHz, the LC tank being further tuned to provide approximately 1 kOhm of impedance when exposed to the first external magnetic field and the second external magnetic field.

19. The implantable medical device of claim 18, the pulse generator including a damping circuit configured to dampen electrical energy imparted to the conductor by the external magnetic field.

20. The implantable medical device of claim 18, further comprising labeling describing the implantable medical device as MRI safe.

\* \* \* \* \*